US009976123B2

(12) United States Patent
Lancaster et al.

(10) Patent No.: US 9,976,123 B2
(45) Date of Patent: May 22, 2018

(54) CELLULAR SEEDING AND CO-CULTURE OF A THREE DIMENSIONAL FIBROBLAST CONSTRUCT

(71) Applicants: Arizona Board of Regents on behalf of the University of Arizona, Tucson, AZ (US); The United States Government as Represented by The Department of Veterans Affairs, Department of Vet, Washington, DC (US)

(72) Inventors: Jordan Lancaster, Tucson, AZ (US); Steve Goldman, Tucson, AZ (US)

(73) Assignees: ARIZONA BOARD OF REGENTS ON BEHALF OF THE UNIVERSITY OF ARIZONA, Tucson, AZ (US); THE UNITED STATES OF AMERICA AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 43 days.

(21) Appl. No.: 14/718,309

(22) Filed: May 21, 2015

(65) Prior Publication Data
US 2015/0328367 A1 Nov. 19, 2015

Related U.S. Application Data

(62) Division of application No. 13/260,610, filed as application No. PCT/US2010/030579 on Apr. 9, 2010, now Pat. No. 9,051,550.

(60) Provisional application No. 61/212,280, filed on Apr. 9, 2009.

(51) Int. Cl.
*A61K 35/34* (2015.01)
*A61K 35/33* (2015.01)
*C12N 5/077* (2010.01)
*A61K 45/06* (2006.01)
*A61L 27/36* (2006.01)
*A61L 27/38* (2006.01)
*C12N 5/00* (2006.01)

(52) U.S. Cl.
CPC ............ *C12N 5/0657* (2013.01); *A61K 35/33* (2013.01); *A61K 35/34* (2013.01); *A61K 45/06* (2013.01); *A61L 27/3604* (2013.01); *A61L 27/367* (2013.01); *A61L 27/3826* (2013.01); *C12N 5/0062* (2013.01); *A61L 2300/64* (2013.01); *A61L 2430/20* (2013.01); *C12N 2502/1323* (2013.01); *C12N 2502/28* (2013.01)

(58) Field of Classification Search
CPC .... C12N 5/0657; C12N 5/0062; A61K 35/33; A61K 35/34; A61L 2430/20; A61L 27/3604; A61L 27/367; A61L 27/3826
See application file for complete search history.

(56) References Cited

U.S. PATENT DOCUMENTS

| | | | |
|---|---|---|---|
| 4,359,049 A | 11/1982 | Redl et al. | |
| 4,414,971 A | 11/1983 | Chung | |
| 4,627,879 A | 12/1986 | Rose et al. | |
| 4,787,900 A | 11/1988 | Yannas | |
| 4,874,368 A | 10/1989 | Miller et al. | |
| 5,290,552 A | 3/1994 | Sierra et al. | |
| 5,318,524 A | 6/1994 | Morse et al. | |
| 5,368,563 A | 11/1994 | Lonneman et al. | |
| 5,521,191 A | 5/1996 | Greenwald | |
| 5,605,541 A | 2/1997 | Holm | |
| 5,613,982 A | 3/1997 | Goldstein | |
| 5,643,192 A | 7/1997 | Hirsh et al. | |
| 5,702,343 A | 12/1997 | Alferness | |
| 5,709,854 A | 1/1998 | Griffith-Cima et al. | |
| 5,759,171 A | 6/1998 | Coelho et al. | |
| 5,763,267 A | 6/1998 | Kurjan et al. | |
| 5,785,964 A | 7/1998 | Naughton et al. | |
| 5,843,766 A | 12/1998 | Applegate et al. | |
| 5,957,972 A | 9/1999 | Williams et al. | |
| 6,077,218 A | 6/2000 | Alferness | |
| 6,085,754 A | 7/2000 | Alferness et al. | |
| 6,126,590 A | 10/2000 | Alferness | |
| 6,155,972 A | 12/2000 | Nauertz et al. | |
| 6,169,922 B1 | 1/2001 | Alferness et al. | |
| 6,174,279 B1 | 1/2001 | Girard | |
| 6,230,714 B1 | 5/2001 | Alferness et al. | |
| 6,241,654 B1 | 6/2001 | Alferness | |
| 6,293,906 B1 | 9/2001 | Vanden Hoek et al. | |
| 6,416,459 B1 | 7/2002 | Haindl | |
| 6,425,856 B1 | 7/2002 | Shapland et al. | |
| 6,537,567 B1 | 3/2003 | Niklason | |
| 6,572,533 B1 | 6/2003 | Shapland et al. | |
| 6,730,016 B1 | 5/2004 | Cox et al. | |
| 2002/0103122 A1 | 8/2002 | Rosen | |
| 2002/0123809 A1 | 9/2002 | Tai | |
| 2002/0127210 A1 | 9/2002 | Mickle et al. | |
| 2002/0160033 A1 | 10/2002 | Caplice | |
| 2002/0182241 A1 | 12/2002 | Borenstein | |
| 2003/0003089 A1 | 1/2003 | Akins et al. | |
| 2003/0007954 A1 | 1/2003 | Naughton et al. | |
| 2003/0113301 A1 | 6/2003 | Edge | |
| 2003/0123026 A1 | 7/2003 | Abitbol | |
| 2003/0216811 A1 | 11/2003 | Badylak | |

(Continued)

FOREIGN PATENT DOCUMENTS

| | | |
|---|---|---|
| EP | 1930411 | 6/2008 |
| WO | 9608213 | 3/1996 |

(Continued)

OTHER PUBLICATIONS

Li et al., Survival and function of bioengineered cardiac grafts. Circulation, vol. 100 (1999) pp. II-63 to II-69.*

(Continued)

*Primary Examiner* — Kara Johnson
(74) *Attorney, Agent, or Firm* — Casimir Jones, S.C.; Robert A. Goetz

(57) ABSTRACT

The present invention provides methods for cellular seeding onto three-dimensional fibroblast constructs, three-dimensional fibroblast constructs seeded with muscle cells, and uses therefore.

17 Claims, 11 Drawing Sheets

(56) References Cited

U.S. PATENT DOCUMENTS

| | | |
|---|---|---|
| 2003/0216812 A1 | 11/2003 | Badylak |
| 2003/0229261 A1 | 12/2003 | Girard et al. |
| 2003/0229265 A1 | 12/2003 | Girard et al. |
| 2004/0006395 A1 | 1/2004 | Badylak |
| 2004/0082063 A1 | 4/2004 | Deshpande et al. |
| 2004/0126879 A1 | 7/2004 | Schneider |
| 2004/0197907 A1 | 10/2004 | Kataoka |
| 2004/0242469 A1 | 12/2004 | Lee |
| 2004/0243170 A1 | 12/2004 | Suresh et al. |
| 2005/0004428 A1 | 1/2005 | Cox |
| 2005/0004485 A1 | 1/2005 | Crosby et al. |
| 2005/0021234 A1 | 1/2005 | Han et al. |
| 2005/0042254 A1 | 2/2005 | Freyman et al. |
| 2005/0090437 A1 | 4/2005 | Nuttall |
| 2005/0142613 A1 | 6/2005 | Bar-Or et al. |
| 2005/0276864 A1 | 12/2005 | LeTort |
| 2006/0154365 A1 | 7/2006 | Ratcliffe et al. |
| 2006/0198827 A1 | 9/2006 | Levenberg |
| 2006/0204441 A1 | 9/2006 | Atala |
| 2006/0228389 A1 | 10/2006 | Li |
| 2006/0292125 A1 | 12/2006 | Kellar et al. |
| 2007/0014772 A1 | 1/2007 | Cohen et al. |
| 2007/0014773 A1 | 1/2007 | Matheny |
| 2007/0092492 A1* | 4/2007 | Matsuda ............ A61L 27/3834 424/93.7 |
| 2007/0258958 A1 | 11/2007 | Ghosh |
| 2008/0050347 A1 | 2/2008 | Ichim |
| 2008/0075750 A1* | 3/2008 | Akins, Jr. ............ A61K 35/34 424/423 |
| 2008/0145344 A1 | 6/2008 | Deshpande et al. |
| 2008/0213230 A1 | 9/2008 | Phillips |
| 2008/0267921 A1 | 10/2008 | Marban |
| 2008/0279830 A1 | 11/2008 | Hoeffler |
| 2009/0035858 A1 | 2/2009 | Bayon |
| 2009/0169521 A1 | 7/2009 | Levenberg |
| 2009/0220565 A1 | 9/2009 | Guldner |
| 2009/0269316 A1 | 10/2009 | Naughton et al. |
| 2010/0055791 A1 | 3/2010 | Morita |
| 2010/0183565 A1 | 7/2010 | Laflamme |
| 2010/0196444 A1 | 8/2010 | Dahlquist |
| 2016/0256497 A1 | 9/2016 | Siani-Rose et al. |

FOREIGN PATENT DOCUMENTS

| | | |
|---|---|---|
| WO | 9749434 A2 | 12/1997 |
| WO | 9900152 | 1/1999 |
| WO | 0034442 | 6/2000 |
| WO | 0035372 | 6/2000 |
| WO | 0061204 | 10/2000 |
| WO | 02058588 | 8/2002 |
| WO | 03061455 | 7/2003 |
| WO | 2004030706 | 4/2004 |
| WO | 2004101735 | 11/2004 |
| WO | 2006001778 | 1/2006 |
| WO | 2005094729 | 10/2006 |
| WO | 2009099570 | 8/2009 |
| WO | 2010011407 | 1/2010 |
| WO | 2010012127 | 2/2010 |
| WO | 2010118352 | 10/2010 |

OTHER PUBLICATIONS

Améen, C., et al. (2008), Critical Reviews in Oncology/Hematology, "Human embryonic stem cells: Current technologies and emerging industrial applications." 65(1), 54-80.

Barile et al., Nat. Clin. Prac. Cardiovasc. Med. Feb. 4, 2007, Suppl 1: S9-S14.

Ben-Shoshan, J. and J. George (2007). "Endothelial progenitor cells as therapeutic vectors in cardiovascular disorders: From experimental models to human trials." Pharmacology & Therapeutics 115(1): 25-36.

Christman, K. L. and R. J. Lee (2006). "Biomaterials for the Treatment of Myocardial Infarction." Journal of the American College of Cardiology 48(5): 907-913.

Dar, A., M. Shachar, et al. (2002). "Cardiac tissue engineering Optimization of cardiac cell seeding and distribution in 3D porous alginate scaffolds." Biotechnology and bioengineering 80(3): 305-312.

Fitzpatrick, J. R., et al. (2010). "Tissue-engineered pro-angiogenic fibroblast scaffold improves myocardial perfusion and function and limits ventricular remodeling after infarction." The Journal of Thoracic and Cardiovascular Surgery 140(3): 667-676.

Freshney, (1987), "A Manual of Basic Technique." Culture of Animal Cells, 2d Ed., Ch. 9, pp. 107-126.

Freshney, (1987), "A Manual of Basic Techniques." Culture of Animal Cells, 2d Ed., Ch. 11 and 12, pp. 137-168.

Gangatirkar, et al. (2007), "Establishment of 3D organotypic cultures using human neonatal epidermal cells." Nature Protocols, 2(1): 178-186.

Guo, et al. (2006). "Engineering Cardiac Tissue from Embryonic Stem Cells." Methods in Enzymology, Academic Press. vol. 420: 316-338.

ISR PCT/US2010/030579, mailed Jul. 12, 2010.

J. Anat. (2006) 209, pp. 527-532.

Kellar, et al. (2001) Circulation, 104(7):2063-2068.

Kellar, et al. (2005) Tissue Engineering, 11(11-12):1678-1687.

Lancaster, et al. (2008). "Treatment of Acute Myocardial Infarction Versus Heart Failure with a Viable 3-Dimensional Fibroblast Patch." Journal of Cardiac Failure 14 (6, Supplement 1): S54-S54.

Lancaster, et al. (2009). "Construction of a Spontaneously Contracting Biologically Active Cardiomyocyte Scaffold." Journal of Cardiac Failure 15(6, Supplement 1): S44-S45.

Lancaster, et al. (2010). "In Vivo Evaluation of a Biologically Active Cardiomyocyte Seeded Scaffold." Journal of Cardiac Failure 16(8, Supplement 1): S45-S45.

Ma, et al. (2009). "Differentiation of bone marrow-derived mesenchymal stem cells into multilayered epidermis-like cells in 3D organotypic coculture." Biomaterials 30(19): 3251-3258.

Martinez, et al. (2010). "Adult stem cells for cardiac tissue engineering." Journal of Molecular and Cellular Cardiology in Press, Corrected Proof.

Maximilian Buja, et al. (2008). "Cardiomyocyte death and renewal in the normal and diseased heart." Cardiovascular Pathology 17(6): 349-374.

Menasché, P. (2008). "Current Status and Future Prospects for Cell Transplantation to Prevent Congestive Heart Failure." Seminars in Thoracic and Cardiovascular Surgery 20(2): 131-137.

Messina, et al., Circulation Research, 2004, 95:911.

Mizuno, et al. (2004). "Hydrostatic fluid pressure promotes cellularity and proliferation of human dermal fibroblasts in a three-dimensional collagen gel/sponge." Biochemical Engineering Journal 20(2-3): 203-208.

Newton et al., 2002, J Foot Ankle Surg, 41(4):233-7).

Noort et al., Pediatric Cardiology, 30(5):699 (2009).

Pullens, et al. (2009). "The influence of endothelial cells on the ECM composition of 3D engineered cardiovascular constructs." Journal of tissue engineering and regenerative medicine 3(1): 11-18.

Radisic, et al. (2008). "Pre treatment of synthetic elastomeric scaffolds by cardiac fibroblasts improves engineered heart tissue." Journal of Biomedical Materials Research Part A 86(3): 713-724.

Radisic, al. et al (2003). "High-density seeding of myocyte cells for cardiac tissue engineering." Biotechnology and bioengineering 82(4): 403-414.

Rennekampff, et al. (1996). "Integrin and matrix molecule expression in cultured skin replacements." Journal of Burn Care & Research 17(3): 213.

Schmidt, et al. (2006). "Mesenchymal stem cells transmigrate over the endothelial barrier." European Journal of Cell Biology 85(11): 1179-1188.

Shapira-Schweitzer, et al. (2009). "A photopolymerizable hydrogel for 3-D culture of human embryonic stem cell-derived cardiomyocytes and rat neonatal cardiac cells." Journal of Molecular and Cellular Cardiology 46(2): 213-224.

(56) References Cited

OTHER PUBLICATIONS

Takei, et al. (1993). "Thermal expansion behavior of skeletonized 3D-composites." Materials Science and Engineering: A 161(2): 213-220.

Thai, et al. (2007). "The Use of a Viable, Biodegradable 3-Dimensional Fibroblast Construct (3DFC) in Acute and Chronic Heart Failure." Journal of Cardiac Failure 13(6, Supplement 2): S121-S121.

Uchino, et al. (2009). "Reconstruction of three-dimensional human skin model composed of dendritic cells, keratinocytes and fibroblasts utilizing a handy scaffold of collagen vitrigel membrane." Toxicology in Vitro 23(2): 333-337.

Wang, et al. (2010). "Cellular cardiomyoplasty and cardiac tissue engineering for myocardial therapy." Advanced Drug Delivery Reviews 62(7-8): 784-797.

Wu, et al. (2007). "Stem cells for tissue engineering of myocardial constructs." Ageing Research Reviews 6(4): 289-301.

Dar et al., "Optimization of cardiac cell seeding and distribution in 3D porous alginate scaffold" Cardiac Tissue Engineering (2002) vol. 80(3), pp. 305-312.

Matsui et al., "Akt activation preserves cardiac function and prevents injury after transient cardiac ischemia in vivo" Circulation (2001) vol. 104, pp. 330-335.

Carrier et al., "Cardiac tissue engineering: cell seeding, cultivation parameters, and tissue, construct characterization" Biotechnology and Bioengineering (1999) vol. 64(5), pp. 580-589.

Radisic et al., "Pre-treatment of synthetic elastomeric scaffolds by cardiac fibroblasts improves engineered heart tissue" Journal of Biomedical Materials Research Part A. (2008) vol. 83(6), pp. 713-724.

Shiba, et al., "Cardiac Applications for Human Pluripotent stem cells," Current pharmaceutical Design, 15(24): 2791-2806, Aug. 2009.

Zakharova, et al., "Transplantation of cardiac progenitor cell sheet onto infarcted heart promotes cardiogenesis and improves function," Cardiovascular Research, 87(1): 40-49, Jan. 2010.

\* cited by examiner

CELLULAR SEEDING AND CO-CULTURE OF A THREE DIMENSIONAL FIBROBLAST CONSTRUCT

RELATED APPLICATIONS

This application is a divisional of U.S. application Ser. No. 13/260,610, filed Feb. 7, 2012, which is a U.S national stage application of PCT Application No. PCT/US10/30579 filed Apr. 9, 2010, which claims the benefit of U.S. Provisional Patent Application Ser. No. 61/212,280 filed Apr. 9, 2009, incorporated by reference herein in its entirety.

STATEMENT OF GOVERNMENT RIGHTS

This invention was made with government support under Merit Review Grant #0128, awarded by the U.S. Department of Veterans Affairs. The government has certain rights in the invention.

SEQUENCE LISTING STATEMENT

The sequence listing is filed in this application in electronic format only and is incorporated by reference herein. The sequence listing text file "10-214-PCTseqlist_ST25.txt" was created on Apr. 9, 2010, and is 32,609 byte in size.

BACKGROUND

New treatments are needed for patients with chronic heart failure (CHF), the No. 1 hospital discharge diagnosis in patients over the age of 65 years of age in this country, as well as related ischemic and non-ischemic cardiac disorders. The prevalence of heart failure is over 5 million; the incidence is 550,000 patients per year. Heart failure results in more deaths than cancer, accidents, and strokes combined, costing more than $23 billion annually. Once a patient becomes symptomatic with NY Class III or IV heart failure, their mortality approaches 50% in two years without a heart transplant. The newest approach to treat CHF is to inject stem cells and/or progenitor cells directly into the heart using a number of different cell types. However, the results from recent clinical trials using such injection strategies are generally disappointing.

SUMMARY OF THE INVENTION

In a first aspect, the present invention provides constructs comprising muscle cells adhered to a 3DFC, wherein the construct is capable of spontaneous synchronized contractions across the 3DFC; and wherein the muscle cells are seeded on the construct at a density of between $0.5 \times 10^6$ cells/cm$^2$ and $5 \times 10^6$ cells/cm$^2$ and/or the muscle cells are present in a ratio of between about 1:10 and about 10:1 with fibroblasts on the 3DFC. In one embodiment, the muscle cells comprise cardiomyocytes or cardiac stem cells.

In a second aspect, the present invention provides methods for treating a disorder characterized by a lack of functioning cardiomyocytes, comprising contacting the heart of a subject suffering from such a disorder with an amount effective to treat the disorder of a construct of any embodiment of the first aspect of the invention. In various embodiments, the disorder is selected from the group consisting of chronic heart failure (CHF), ischemia without heart failure, cardiomyopathy (such as dilated cardiomyopathy (DCM)), cardiac arrest, congestive heart failure, stable angina, unstable angina, myocardial infarction, coronary artery disease, valvular heart disease, ischemic heart disease, reduced ejection fraction, reduced myocardial perfusion, maladaptive cardiac remodeling (such as left ventricle remodeling), reduced left ventricle function, left heart failure, right heart failure, backward heart failure (increased venous back pressure), forward heart failure (failure to supply adequate arterial perfusion), systolic dysfunction, diastolic dysfunction, systemic vascular resistance, low-output heart failure, high-output heart failure, dyspnea on exertion, dyspnea at rest, orthopnea, tachypnea, paroxysmal nocturnal dyspnea, dizziness, confusion, cool extremities at rest, exercise intolerance, easy fatigueability, peripheral edema, nocturia, ascites, hepatomegaly, pulmonary edema, cyanosis, laterally displaced apex beat, gallop rhythm, heart murmurs, parasternal heave, and pleural effusion.

In a third aspect, the present invention provides methods for seeding a three dimensional fibroblast construct (3DFC) with cells, comprising:

(a) contacting a cultured 3DFC with a suspension of cells to be seeded onto the 3DFC;

(b) subjecting the cells within the suspension to a force that causes said cells to contact the 3DFC; and (c) culturing the cells under conditions suitable for the cells to adhere to the 3DFC.

In a fourth aspect, the present invention provides methods for seeding a three dimensional fibroblast construct (3DFC) with cells, comprising:

(a) contacting a cultured 3DFC with a cell sheet to be seeded onto the 3DFC; and (b) culturing the cell sheet under conditions suitable for the cell sheet to adhere to the 3DFC.

In a fifth aspect, the present invention provides constructs of any embodiment of the first aspect of the invention made using the methods of any embodiment of the third or fourth aspects of the invention.

BRIEF DESCRIPTION OF THE FIGURES

FIG. 4: 40× time elapsed images of control (A), NCM-3DFC (B), and NCM-3DFC+halothane (C) treated patches, cultured for 6 days and continuously injected with NBD. (A) Injection of a single fibroblast, note lack of dye transfer. (B) Injection of single neonatal cardiomyocyte on NCM-3DFC spreads to numerous neighboring cells. (C) Injection of a single neonatal cardiomyocyte on NCM-3DFC treated with halothane. Note the disruption of dye transfer due to blockage of connexins by halothane. Cells regain ability to use gap junctions 15 to 20 minutes after halothane treatment.

DETAILED DESCRIPTION OF THE INVENTION

Figure 1:
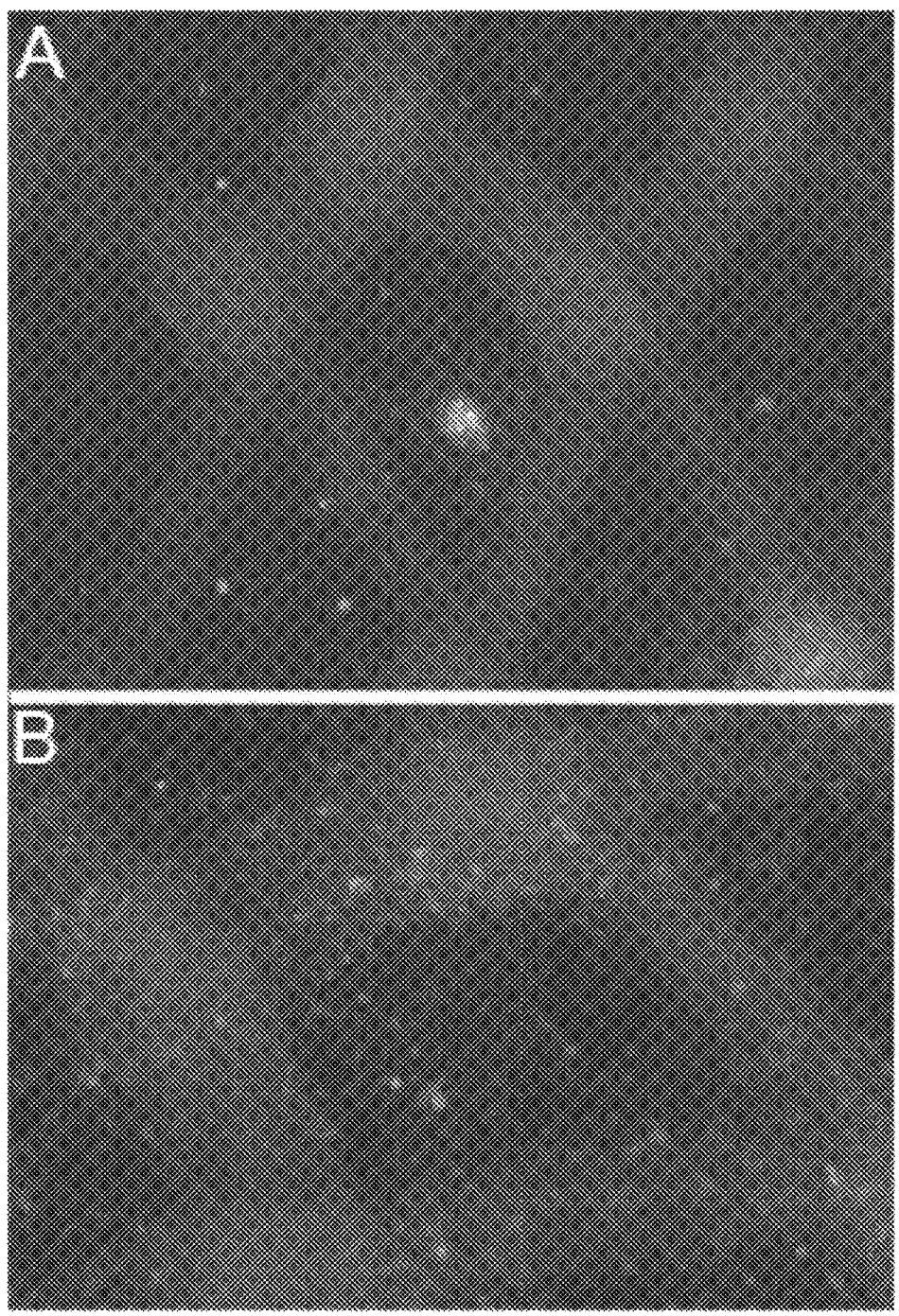
FIG. 1: Endothelial progenitor cells tagged with CFDA-se co-cultured on 3DFC at A) 10 min and B) 24 hrs after seeding. Positively stained CFDA-se tagged cells fluoresce green demonstrating additional cells seeded on the 3DFC survive and proliferate. The biodegradable vicryl mesh can be seen in the background.

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, $2^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

All embodiments disclosed herein can be combined with other embodiments unless the context clearly dictates otherwise.

In a first aspect, the present invention provides methods for seeding a three dimensional fibroblast construct (3DFC) with cells, comprising:
  (a) contacting a cultured 3DFC with a suspension of cells to be seeded onto the 3DFC;
  (b) subjecting the cells within the suspension to a force that causes the cells to contact the 3DFC; and
  (c) culturing the cells under conditions suitable for the cells to adhere to the 3DFC.

The inventors have discovered that cells to be adhered to the 3DFC do not adequately settle out of solution onto the patch and adhere to the 3DFC through cell-surface adhesion molecules. Early attempts at seeding the 3DFC evaluated the placement of cells suspended in culture media with the notion that standard gravitational force would "settle" the desired cells on the 3DFC below. Results found, poor retention of cells on the 3DFC with a majority of cells passing to the culture plate below. The inventors thus developed the methods of this first aspect of the invention to force the cells to adhere to the surface of the 3DFC. Such seeded 3DFC can be used, for example, in cell-based therapies, as described in detail below.

As used herein, a "three dimensional fibroblast construct" is a construct comprising fibroblasts grown on a three-dimensional substrate comprising a biocompatible, non-living material formed into a three-dimensional structure having interstitial spaces bridged by the cells in the construct. It will be understood that the 3DFC may contain cell types in addition to fibroblasts as appropriate for a given purpose. For example, the 3DFC may also comprise other stromal cells, including but not limited to endothelial cells. See, for example, published US patent application US2009/0269316 and U.S. Pat. No. 4,963,489, both incorporated by reference herein in their entirety.

The fibroblasts and other cells may be fetal or adult in origin, and may be derived from convenient sources such as skin, cardiac muscle, smooth muscle, skeletal muscle, liver, pancreas, brain, adipose tissue (fat) etc. Such tissues and or organs can be obtained by appropriate biopsy or upon autopsy. In alternative embodiments for all aspects of the invention, the fibroblasts and other cells are human cells. In an alternative embodiment for all aspects of the invention, the 3DFC is a matrix-embedded human dermal construct of newborn dermal fibroblasts cultured in vitro onto a bioabsorbable mesh to produce living, metabolically active tissue. The fibroblasts proliferate across the mesh and secrete a large variety of growth factors and cytokines, including human dermal collagen, fibronectin, and glycosaminoglycans (GAGs), embedding themselves in a self-produced dermal matrix. In culture the fibroblasts produce angiogenic growth factors: VEGF (vascular endothelial growth factor), HGF (hepatocyte growth factor), bFGF (basic fibroblast growth factor), and angiopoietin-1 (See, for example, J. Anat. (2006) 209, pp 527-532)

The cells to be seeded onto the 3DFC may be of any desired type, including but not limited to muscle cells (skeletal muscle cells, smooth muscle cells, cardiac muscle cells such as cardiomyocyte) or progenitors thereof, endothelial progenitor cells, bone marrow cells, bone marrow cells, mesenchymal stem cells, umbilical cord blood cells or combinations thereof. Such cells can be isolated using standard techniques in the art, or may be obtained from commercial sources.

In an alternative embodiment of all aspects of the invention, the seeded cells comprise cardiomyocytes and/or progenitors thereof such as cardiac stem cells. There are a limited number of intrinsic cardiac stem cells in the mature adult heart that are self-renewing, clonogenic, and multipotent, such that they differentiate into cardiomyocytes and, to a lesser extent, into smooth muscle and endothelial cells. Cardiac stem cells can be isolated and expanded in culture indefinitely. In one embodiment, the cardiac stem cells are characterized by cell surface markers: Lin−, c-Kit+, CD45−, CD34−.

The cells to be seeded may be recombinant cells capable of expressing a gene product of interest for a given purpose. In one alternative embodiment as described in more detail below, cardiomyocytes engineered to express one or more of thymosin beta-4 (TB4), akt murine thyoma viral oncogene homolog (AKT1; SEQ ID NO:1, 3, or 5 for amino acid sequence), stroma cell-derived factor-1 alpha (SDF-1; SEQ ID NO:7 for amino acid sequence), and hepatocyte growth factor (HGF; SEQ ID NO:9 for amino acid sequence) are seeded onto the 3DFC. Techniques for engineering cells to express a heterologus gene product are well known in the art, and utilize cell transfection by recombinant expression vector that operatively link a nucleic acid coding region or gene to any promoter capable of effecting expression of the gene product. Thus, in various embodiments, the cells comprise a recombinant expression vector encoding a nucleic acid sequence that encodes the polypeptide sequence one or more of SEQ ID NO:1, 3, 5, 7, 9, and 11, In various further embodiments, the nucleic acid sequence is selected from the group consisting of SEQ ID NOS: 2, 4, 6, 8, and 10. The promoter sequence used to drive expression of the disclosed nucleic acid sequences in a mammalian system may be constitutive (driven by any of a variety of promoters, including but not limited to, CMV, SV40, RSV, actin, EF, etc.) or inducible (driven by any of a number of inducible promoters including, but not limited to, tetracycline, ecdysone, steroid-responsive). See, for example, Sambrook, Fritsch, and Maniatis, in: Molecular Cloning, A Laboratory Manual, Cold Spring Harbor Laboratory Press, 1989; *Gene Transfer and Expression Protocols*, pp. 109-128, ed. E. J. Murray, The Humana Press Inc., Clifton, N.J.), and the Ambion 1998 Catalog (Ambion, Austin, Tex.).

Contacting a cultured 3DFC with a suspension of cells to be seeded onto the 3DFC can be done under any suitable conditions to facilitate application of the force that causes the cells to contact the 3DFC, including but not limited to the conditions described below. In one alternative embodiment, the 3DFC is placed in 0.1 to 5 ml of media (preferably 0.25 ml-2 ml, and more preferable 0.5 ml-1.0 ml of media), and cells are introduced in suspension, such that the volume of cell suspension is approximately double the volume of media in which the 3DFC is placed. In one alternative embodiment that can be combined with any other embodiments herein, the contacting occurs at approximately 37° C. In a further alternative embodiment that can be combined with any other embodiments herein, the cell suspension has a concentration of at least $3 \times 10^6$ cells/ml where the cells to be seeded are contractile cells (such as cardiomyocytes or progrenitors thereof). In further alternative embodiments that can be combined with any other embodiments herein, the cell suspension has a concentration of at least $4 \times 10^6$ cells/ml and $5 \times 10^6$ cells/ml.

In one embodiment, each 3DFC to be seeded is placed in a well so as to cover the base of the well and lay flat. The inventors have discovered that if the 3DFC does not cover the base of the well (when seeding 3DFCs placed in wells), a decreased retention of cells occurs, and results in an unequal distribution of cells across the patch due to cell bunching and clumping.

Subjecting the cells within the suspension to a force that causes said cells to contact the 3DFC may comprise the use of any suitable force, including but not limited to a centrifugal force and an electrical force generated by an electric field, or combinations of such forces. In an alternative embodiment, a centrifugal force is used. The centrifugal force to be applied depends on a variety of factors, such as the cell type to be seeded onto the 3DFC. In one alternative embodiment that can be combined with any other embodiments herein, the construct is centrifuged at between 1200 rpms and 1600 rpms for between 2 and 10 minutes. In an alternative embodiment, all 3DFC constructs to be seeded are placed in a horizontal arrangement in wells (as opposed to vertical), so that each well is spun at the same radius.

In one alternative embodiment, the force may be applied within 0-300 seconds after contacting of the cell suspension with the 3DFC in appropriate culture medium.

It will be understood by those of skill in the art that it is not a requirement that all cells in the suspension contact the 3DFC as a result of the force application, as the cells can preferably be present in the suspension in an amount that saturates all available locations for seeding onto the 3DFC. In one alternative embodiment, the seeded cells contact each other, such that multiple cell layers are provided on top of the 3DFC. In embodiments where cardiomyocytes or precursors thereof are used, it is preferred that the seeded cells reside in the "valleys" between fibers on the 3DFC (see below for description of 3DFC structure). Exemplary images of such cardiomyocyte-seeded 3DFCs are shown in FIGS. 8-11.

Culturing the cells under conditions suitable for the cells to adhere to the 3DFC may comprise the use of any culture media and conditions suitable for a given purpose, such as those in the examples that follow. Any useful media may be used, including but not limited to DMEM-LG supplemented with fetal bovine serum (5-15%; preferably 10%) and other appropriate factors (including but not limited to sodium bicarbonate and antibiotics. It will be understood by those of skill in the art that it is not a requirement that all cells in the suspension adhere to the 3DFC as a result of the force application, as the cells can preferably be present in the suspension in an amount that saturates all available locations for adherence onto the 3DFC. In an alternative embodiment that can be combined with any other embodiment disclosed herein, the cells are adhered to the 3DFC at a cell density ranging between $0.5 \times 10^6$ cells/cm$^2$ and $5 \times 10^6$ cells/cm$^2$; more preferably between $1 \times 10^6$ cells/cm$^2$ and $4 \times 10^6$ cells/cm$^2$; and most preferably between $1.5 \times 10^6$ cells/cm$^2$ and $3 \times 10^6$ cells/cm$^2$.

In a further alternative embodiment that can be combined with any of the other embodiments disclosed herein, the culturing further comprises growth of cells adhered to the 3DFC. In this embodiment, such growth can occur under the same or different culture conditions than those used to promote adherence of the suspended cells to the 3DFC. Suitable culture conditions to promote proliferation and/or differentiation of cells adhered to the 3DFC can be determined by those of skill in the art, based on the disclosure herein.

In another alternative embodiment that can be combined with any other embodiment herein, the seeded 3DFCs are incubated within 5 minutes of application of force and not disturbed (i.e. the 3DFCs are not removed from culture plate, media changed, etc.). Seeded 3DFCs for in vivo implant are preferably harvested from culture plates ~18-20 hrs after seeding/incubation.

Exemplary methods for seeding are provided in the examples that follow. The 3DFC may be purchased from commercial sources (ANGINERA™ (Theregen, Inc., California); Advanced BioHealing, Inc (DERMAGRAFT®)), or may be prepared as described, for example, in US2009/0269316 and U.S. Pat. No. 4,963,489. Briefly, fibroblasts and, optionally, other stromal cells as deemed appropriate for a given purpose, are inoculated upon a three-dimensional framework, and grown to develop the 3DFC. The fibroblasts and other stromal cells may be engineered to express gene products of interest, such as thymosin beta 4. See, for example, U.S. Pat. Nos. 5,785,964 and 5,957,972, incorporated by reference herein in their entirety.

The three-dimensional support framework may be of any material and/or shape that: (a) allows cells to attach to it (or can be modified to allow cells to attach to it); and (b) allows cells to grow in more than one layer. A number of different materials may be used to form the framework, including but not limited to: nylon (polyamides), dacron (polyesters), polystyrene, polypropylene, polyacrylates, polyvinyl compounds (e.g., polyvinylchloride; PVC), polycarbonate, polytetrafluorethylene (PTFE; TEFLON), thermanox (TPX), nitrocellulose, cotton, polyglycolic acid (PGA), cat gut sutures, cellulose, gelatin, dextran, etc. Any of these materials may be woven into a mesh to form the three-dimensional framework. Certain materials, such as nylon, polystyrene, etc., are poor substrates for cellular attachment. When these materials are used as the three-dimensional support framework, it is advisable to pre-treat the framework prior to inoculation of fibroblasts and other stromal cells in order to enhance their attachment to the framework. For example, prior to inoculation with fibroblasts and other stromal cells, nylon screens could be treated with 0.1 M acetic acid, and incubated in polylysine, fetal bovine serum, and/or collagen to coat the nylon. Polystyrene could be similarly treated using sulfuric acid.

When the 3DFC is to be implanted directly in vivo, it may be preferable to use biodegradable materials such as PGA, catgut suture material, collagen, polylactic acid, or hyaluronic acid. For example, these materials may be woven into a three-dimensional framework such as a collagen sponge or collagen gel. Where the cultures are to be maintained for long periods of time or cryopreserved, non-degradable materials such as nylon, dacron, polystyrene, polyacrylates, polyvinyls, teflons, cotton, etc. may be preferred. A convenient nylon mesh which could be used in accordance with the invention is a nylon filtration mesh having an average pore size of 140 µm and an average nylon fiber diameter of 90 µm (#3-210/36, Tetko, Inc., N.Y.).

Stromal cells comprising fibroblasts, with or without other cells and elements described below, are inoculated onto the framework. These stromal cells may be derived from tissues or organs, such as skin, heart, blood vessels, skeletal muscle, liver, pancreas, brain etc., which can be obtained by biopsy (where appropriate), from surgically obtained specimens, or upon autopsy. Fetal fibroblasts can be used to form a "generic" three-dimensional stromal tissue that will support the growth of a variety of different cells and/or tissues that come in contact with it. However, a "specific" stromal tissue may be prepared by inoculating the three-dimensional framework with stromal cells derived from the heart and/or from a particular individual who is later to receive the cells and/or tissues grown in culture in accordance with the present invention. Such samples can be obtained, for example, through standard biopsy procedures (such as a myocardial biopsy when stromal cells from the heart are to be obtained) or other surgical procedure.

Stromal cells may be readily isolated by disaggregating an appropriate organ or tissue. This may be readily accomplished using techniques known to those skilled in the art. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include, but are not limited to, trypsin, chymotrypsin, collagenase, elastase, and/or hyaluronidase, DNase, pronase, and dispase. Mechanical disruption can also be accomplished by a number of methods including, but not limited to, the use of grinders, blenders, sieves, homogenizers, pressure cells, or insonators to name but a few. For a review of tissue disaggregation techniques, see Freshney, Culture of Animal Cells. A Manual of Basic Technique, 2d Ed., A.R. Liss, Inc., New York, 1987, Ch. 9, pp. 107-126.

Once the tissue has been reduced to a suspension of individual cells, the suspension can be fractionated into subpopulations from which the fibroblasts and/or other stromal cells and/or elements can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counter-streaming centrifugation), unit gravity separation, countercurrent distribution, electrophoresis and fluorescence-activated cell sorting. For a review of clonal selection and cell separation techniques, see Freshney, Culture of Animal Cells. A Manual of Basic Techniques, 2d Ed., A.R. Liss, Inc., New York, 1987, Ch. 11 and 12, pp. 137-168.

Where the cultured cells are to be used for transplantation or implantation in vivo, it is preferable to obtain the stromal cells from the patient's own tissues.

After inoculation of the stromal cells, the 3DFC should be incubated in an appropriate nutrient medium. Many commercially available media such as RPMI 1640, Fisher's, Iscove's, McCoy's, and the like may be suitable for use. In an alternative embodiment, the 3DFC may be suspended in the medium during the incubation period in order to maximize proliferative activity of the fibroblasts and other stromal cells. In addition, the culture should be "fed" periodically to remove the spent media, depopulate released cells, and add fresh media. During the incubation period, the fibroblasts and other stromal cells will grow linearly along and envelop the filaments of the three-dimensional framework before beginning to grow into the openings of the framework.

The openings of the framework should be of an appropriate size to allow the fibroblasts and other stromal cells to stretch across the openings. Maintaining actively growing stromal cells that stretch across the framework enhances the production of growth factors that are elaborated by the stromal cells, and hence will support long term cultures. For example, if the openings are too small, the stromal cells may rapidly achieve confluence but be unable to easily exit from the mesh; trapped cells may exhibit contact inhibition and cease production of the appropriate factors necessary to support proliferation and maintain long term cultures. If the openings are too large, the stromal cells may be unable to stretch across the opening; this will also decrease stromal cell production of the appropriate factors necessary to support proliferation and maintain long term cultures. When using a mesh type of framework, as exemplified herein, it has been found that openings ranging from about 140 µm to about 220 µm will work satisfactorily. However, depending upon the three-dimensional structure and intricacy of the framework, other sizes may work equally well. In fact, any shape or structure that allows the stromal cells to stretch and continue to replicate and grow for lengthy time periods will work in accordance with the invention.

Different proportions of the various types of collagen deposited on the framework can affect the growth of the cells that come in contact with the 3DFC. The proportions of extracellular matrix (ECM) proteins deposited can be manipulated or enhanced by selecting fibroblasts that elaborate the appropriate collagen type. This can be accomplished using monoclonal antibodies of an appropriate isotype or subclass that are capable of activating complement, and which define particular collagen types. These antibodies and complement can be used to negatively select the fibroblasts which express the desired collagen type. Alternatively, the stroma used to inoculate the framework can be a mixture of cells which synthesize the appropriate collagen types desired. Thus, since the 3DFC described herein is suitable for the growth of diverse cell types and tissues, and depending upon the tissue to be cultured and the collagen types desired, the appropriate stromal cell(s) may be selected to inoculate the three-dimensional framework.

During incubation of the 3DFC, proliferating cells may be released from the framework. These released cells may stick to the walls of the culture vessel where they may continue to proliferate and form a confluent monolayer. This should be prevented or minimized, for example, by removal of the released cells during feeding, or by transferring the 3DFC to a new culture vessel. The presence of a confluent monolayer in the vessel may "shut down" the growth of cells in the 3DFC. Removal of the confluent monolayer or transfer of the stromal tissue to fresh media in a new vessel will restore proliferative activity of the 3DFC. Such removal or transfers should be done in any culture vessel which has a stromal monolayer exceeding 25% confluency. Alternatively, the 3DFC could be agitated to prevent the released cells from sticking, or instead of periodically feeding the cultures, the culture system could be set up so that fresh media continuously flows through the 3DFC. The flow rate could be adjusted to both maximize proliferation within the 3DFC, and to wash out and remove cells released from the culture, so that they will not stick to the walls of the vessel and grow to confluence.

In a second aspect, the present invention provides methods for seeding a three dimensional fibroblast construct (3DFC) with cells, comprising:

(a) contacting a cultured 3DFC with a cell sheet to be seeded onto the 3DFC; and (b) culturing the cell sheet under conditions suitable for the cell sheet to adhere to the 3DFC.

The inventors have unexpectedly discovered that the methods of this aspect of the invention permit the harvest of cells sheets for seeding onto a 3DFC, and thus permit their use as a delivery method, such as the methods disclosed below for treating chronic heart failure.

In one alternative embodiment, cell sheets with cardiac stem cells are adhered to the 3DFC, allowing cardiac stem cells to establish and maintain cellular/electrical communications such as gap junctions prior to placement onto the myocardium in the methods of the invention for treating CHF, discussed in more detail below.

All terms in this second aspect are as defined for the first aspect of the invention, and all embodiments of the first aspect of the invention are equally applicable to this second aspect of the invention. In this second aspect, the 3DFC is contacted with a cell sheet under conditions suitable for adherence to the 3DFC. As used herein, a "cell sheet" comprises confluent cells dissociated from culture as an intact "sheet" for contacting with the 3DFC. In an alternative embodiment, the disassociating is effected by chilling the culture substrate to a temperature effective to release said cells as an intact cell sheet; any suitable temperature may be used, preferably between 10-20° C.

Contacting a cultured 3DFC with a cell sheet to be seeded onto the 3DFC and subsequent culturing to promote cell sheet adherence to the 3DFC can be done under any suitable conditions, such as those described in the examples that follow, and those discussed with respect to the first aspect of the invention. Based on the teachings herein, those of skill in the art can determine appropriate conditions for contacting the cultured 3DFC with the cell sheet to be seeded onto the 3DFC; and culturing the cell sheet under conditions suitable for the cell sheet to adhere to the 3DFC. In one exemplary alternative embodiment, the cells of interest are grown in culture until confluency, followed by chilling of the culture substrate to approximately 10° C.-20° C.), which allows dissociation of the cell sheet from the culture substrate. Dissociation is generally complete within (30-60 minutes, and the dissociated cell sheet is taken up by any suitable means, such as by appropriately sized pipette and transferred onto the 3DFC. In one alternative embodiment, a suitable amount of culture media (1-5 µl; preferably 2-3 ul) is placed onto the cell sheet so that it unfolds to lay flat against the 3DFC. Any suitable cell media may be used, including but not limited to DMEM supplemented with 5-15% fetal bovine serum (preferably approximately 10%). After the cell sheet is relatively flattened and is flush against the 3DFC excess media is removed using a pipette. The 3DFC cell sheet complex is placed in the incubator for 5 min at 5.0% $CO_2$ and 37 degrees C. After which, the 3DFC cell sheet complex is re-suspended in 37 degree C. 10% FBS in DMEM and cultured overnight. The cell sheet is preferably centrally placed on the 3DFC, and is placed so as to minimize folds or bunching in the cell sheet. The construct is then incubated under appropriate conditions to promote adhesion of the cells in the cell sheet to the 3DFC. Any suitable conditions can be used. In one alternative embodiment that can be combined with any other embodiments herein, the incubation occurs at 37° C. and 5% $CO_2$ for between 5 and 15 minutes; more preferably between 7.5 and 12.5 minutes; most preferably approximately 10 minutes.

In a further alternative embodiment, the desired cells are grown and cultured in temperature sensitive plates under standard culture conditions. Once confluent, cell media volume is reduced by 50% and the plates are chilled at 20 degrees C. for 30-60 min or until cell sheets dissociate from the culture plate. Using a pipette, cell sheets are harvested, placed on thawed 3DFC and flattened using droplets of standard culture media. Once flattened, excess media is removed using a pipette. The 3DFC cell sheet complex is placed in the incubator (5.0% $CO_2$ at 37° C. for 5 min. 3DFC cell sheet complex is re-suspended in 37° C. standard culture medium, placed back in the incubator and cultured over night. Culture media is changed every 48 hrs.

Any suitable initial seeding densities in the temperature sensitive culture plates can be used, and may vary on cell type. In one alternative embodiment, cardiomyocytes or precursors thereof are seeded at approximately $1-2 \times 10^4$ cells/mm$^2$; preferably approximately $1.4 \times 10^4$ cells/mm$^2$.

The cells in the cell sheet may be of any desired type, including but not limited to muscle cells (skeletal muscle cells, smooth muscle cells, cardiac muscle cells such as cardiomyocyte) and progenitors thereof, endothelial progenitor cells, bone marrow cells, umbilical cord blood cells, and combinations thereof. In an alternative embodiment cell types with strong cell-cell interactions, such as endothelial cells and cardiomyocytes or progenitors thereof, are used.

In an alternative embodiment of all aspects of the invention, the seeded cells comprise cardiomyocytes and/or progenitors thereof such as cardiac stem cells. There are a limited number of intrinsic cardiac stem cells in the mature adult heart that are self-renewing, clonogenic, and multipotent, such that they differentiate into cardiomyocytes and, to a lesser extent, into smooth muscle and endothelial cells. Cardiac stem cells can be isolated and expanded in culture indefinitely and are characterized by cell surface markers: Lin−, c-Kit+, CD45−, CD34−. See, for example, Messina et al., Circulation Research, 2004, 95:911; Barile et al., Nat. Clin. Prac. Cardiovasc. Med. 2007, February 4, Suppl 1: S9-S14; Noort et al., Pediatric Cardiology, 30(5):699 (2009); Cardiac stem cell isolation kit available from Millipore (Cat. #SCR061)

The cells to be seeded may be recombinant cells capable of expressing a gene product of interest for a given purpose. In one alternative embodiment as described in more detail below, cardiomyocytes engineered to express thymosin beta-4 are seeded onto the 3DFC.

It will be understood by those of skill in the art that it is not a requirement that all cells in the cell sheet contact the 3DFC. In one alternative embodiment, the seeded cell sheets may contact each other, to yield two or more cell layers atop the 3DFC. It will be understood by those of skill in the art that it is not a requirement that all cells in the cell sheet adhere to the 3DFC as a result of the force application, as the cells are preferably present in the suspension in an amount that saturates all available locations for adherence onto the 3DFC. In an alternative embodiment that can be combined with any other embodiment disclosed herein, the cells are adhered to the 3DFC at a cell density ranging between $0.5 \times 10^6$ cells/cm$^2$ and $5 \times 10^6$ cells/cm$^2$; more preferably between $1 \times 10^6$ cells/cm$^2$ and $4 \times 10^6$ cells/cm$^2$; and most preferably between $1.5 \times 10^6$ cells/cm$^2$ and $3 \times 10^6$ cells/cm$^2$.

In a further alternative embodiment that can be combined with any of the other embodiments disclosed herein, the culturing further comprises growth of cells adhered to the 3DFC. In this embodiment, such growth can occur under the same or different culture conditions than those used to promote adherence of the cell sheet to the 3DFC. Suitable culture conditions to promote proliferation and/or differentiation of cells adhered to the 3DFC can be determined by those of skill in the art, based on the disclosure herein. Once adhesion of the sheet occurs, the 3DFC cell sheet complex can be cultured under standard culture methods.

In a third aspect, the present invention provides constructs comprising muscle cells adhered to a 3DFC, wherein the cells are capable of spontaneous synchronized contractions across the 3DFC; and wherein the muscle cells are seeded on the construct at a density of between $0.5 \times 10^6$ cells/cm$^2$ and $5 \times 10^6$ cells/cm$^2$ and/or the muscle cells are present in a ratio of between about 1:10 and about 10:1 with fibroblasts on the construct. Terms in this third aspect of the invention retain the meaning disclosed in the first and second aspects of the invention. All embodiments of the first and second aspects of the invention are equally applicable to this third aspect of the invention, unless the context clearly indicates otherwise. In another embodiment, fibroblasts are present on the construct at a density of between about $5.0 \times 10^5$ cells/cm$^2$ and about $5.0 \times 10^6$ cells/cm$^2$; in another embodiment between about $8.0 \times 10^5$ cells/cm$^2$ and about $2.0 \times 10^6$ cells/cm$^2$.

As discussed in more detailed below, the inventors have discovered that the constructs of this aspect of the invention can be used, for example, in cell therapy for treating various disorders such as chronic heart failure. The inventors have further discovered that the resulting construct provides for cell-cell communication across the construct, which can beat synchronously.

In one alternative embodiment, the 3DFC comprises a patch, with the cells seeded onto a top portion of the patch. In this embodiment, the bottom portion of the patch can be attached to a surface of interest, such as the heart.

The constructs of the invention comprise muscle cells are seeded on the construct at a density of between $0.5 \times 10^6$ cells/cm$^2$ and $5 \times 10^6$ cells/cm$^2$ and/or muscle cells are present in a ratio about of between 1:10 and about 10:1 with fibroblasts on the construct. In one embodiment, muscle cells are seeded on the construct at a density of between $1.5 \times 10^6$ cells/cm$^2$ $3.0 \times 10^6$ cells/cm$^2$. In another embodiment, the muscle cells are present in a ratio of between about 1:10 and about 10:1 with fibroblasts on the construct. In another embodiment, the muscle cells are seeded on the construct at a density of between $0.5 \times 10^6$ cells/cm$^2$ and $5 \times 10^6$ and the muscle cells are present in a ratio of between 1:10 and 10:1 with fibroblasts on the construct. In a preferred embodiment of all these embodiments, the muscle cells are cardiomyocytes or precursors thereof.

In various embodiments, the muscle cells (such as cardiomyocytes or precursors thereof) are present in a ratio with fibroblasts on the construct of between about 1:10 and about 10:1; about 1:9 to about 9:1; about 1:8 to about 8:1; about 1:7 to about 7:1; about 1:6 to about 6:1; about 1:5 to about 5:1; about 1:4 to about 4:1; about 1:3 to about 3:1; about 1:2 to about 2:1; or about 1:1. Other ratios of cells are also possible. In a preferred embodiment of all these embodiments, the muscle cells are cardiomyocytes or precursors thereof.

In various embodiments, the muscle cells (such as cardiomyocytes or precursors thereof) are seeded on the construct at a density between $1.3 \times 10^6$ cells/cm$^2$ and $5 \times 10^6$ cells/cm$^2$; more preferably between $1.4 \times 10^6$ cells/cm$^2$ and $4 \times 10^6$ cells/cm$^2$; and most preferably between $1.5 \times 10^6$ cells/cm$^2$ and $3 \times 10^6$ cells/cm$^2$. In a preferred embodiment of all these embodiments, the muscle cells are cardiomyocytes or precursors thereof In another embodiment, the cardiomyocytes or precursors thereof are seeded on the construct at a density between $1.5 \times 10^6$ cells/cm$^2$ and $3 \times 10^6$ cells/cm$^2$, and the fibroblasts are present on the construct at a density of between about $8.0 \times 10^5$ cells/cm$^2$ and about $2.0 \times 10^6$ cells/cm$^2$.

As used herein, "muscle cells" can be skeletal muscle cells, smooth muscle cells, cardiac muscle cells, or precursors thereof. In an alternative embodiment that can be combined with any other embodiment herein, the muscle cells comprise cardiomyocytes or precursors thereof; most preferably of human origin. In a further alternative embodiment that can be combined with any other embodiment, the construct is a seeded, non-contracting patch, which can be ready for implantation by 24 hours after seeding and used, for example, to provide cardiomyocytes to the host heart. In another alternative embodiment that can be combined with any other embodiment, the construct is a contractile construct, is capable of spontaneous synchronized contractions, and may be used, for example, for contractile assistance. As used herein, the phrase "spontaneous synchronized contractions" means that the cells are capable of producing coordinated force generation across the 3DFC. As used herein, "across the 3DFC" means that the cells are capable of spontaneous synchronized contractions over the full 3DFC where the cells are adhered.

In a further alternative embodiment that can be combined with any other embodiment herein, the muscle cells, or precursors thereof, are obtained from a subject (such as by standard biopsy procedures or other surgical procedures) to be treated with the construct in the methods of the invention described below. In a further alternative embodiment that can be combined with any other embodiment herein, the cells can be engineered to express a protein of interest, such as cardiomyocytes or precursors thereof engineered to express one or more of thymosin beta-4 (TB4), akt murine thyoma viral oncogene homolog (AKT1; SEQ ID NO:1, 3, or 5 for amino acid sequence), stroma cell-derived factor-1 alpha (SDF-1; SEQ ID NO:7 for amino acid sequence), and hepatocyte growth factor (HGF; SEQ ID NO:9 for amino acid sequence), as disclosed above.

The constructs can be made shortly prior (ie, 0-10 days prior) to a desired implantation according to the methods of the invention described below, or may be stored frozen and rethawed prior to implantation.

The muscle cells can be adhered to the 3DFC at any density suitable for a given application. In an alternative embodiment that can be combined with any other embodiment disclosed herein, the muscle cells (such as cardiomyocytes or precursors thereof) are adhered to the 3DFC at a cell density ranging between $1.3 \times 10^6$ cells/cm$^2$ and $5 \times 10^6$ cells/cm$^2$; more preferably between $1.4 \times 10^6$ cells/cm$^2$ and $4 \times 10^6$ cells/cm$^2$; and most preferably between $1.5 \times 10^6$ cells/cm$^2$ and $3 \times 10^6$ cells/cm$^2$. Lower density cardiomyocyte seedings ($0.6$-$1.2 \times 10^6$ cells/cm$^2$) displayed non-synchronized yet spontaneous contractions, while higher density constructs disclosed were capable of consistent rhythmic and directional contractions Specific methods for producing constructs according to this aspect of the invention are provided in the examples that follow. In one embodiment, the methods of any embodiment or combination of embodiments of the first or second aspect of the invention can be used to make the constructs of this third aspect. In one alternative embodiment, cell sheets with cardiac stem cells or cardiomyocytes are adhered to the 3DFC, allowing cardiac stem cells or cardiomyocytes to which they give rise to establish and maintain cellular/electrical communications such as gap junctions prior to placement onto the myocardium in the methods of the invention for treating CHF, discussed in more detail below.

In a fourth aspect, the present invention provides methods for treating a disorder characterized by a lack of functioning cardiomyocytes, comprising contacting the heart of a subject suffering from such a disorder with an amount effective to treat the disorder of a construct according to the third aspect of the invention that comprise cardiomyocytes or precursors thereof adhered to a 3DFC.

The inventors have unexpectedly discovered that the constructs of this aspect of the invention can be used, for example, in cell therapy for treating disorders characterized by a lack of functioning cardiomyocytes. Such disorders include, but are not limited to, chronic heart failure (CHF), ischemia without heart failure, cardiomyopathy (such as dilated cardiomyopathy (DCM)), cardiac arrest, congestive heart failure, stable angina, unstable angina, myocardial infarction, coronary artery disease, valvular heart disease, ischemic heart disease, reduced ejection fraction, reduced myocardial perfusion, maladaptive cardiac remodeling (such as left ventricle remodeling), reduced left ventricle function, left heart failure, right heart failure, backward heart failure (increased venous back pressure), forward heart failure (failure to supply adequate arterial perfusion), systolic dysfunction, diastolic dysfunction, systemic vascular resistance, low-output heart failure, high-output heart failure, dyspnea on exertion, dyspnea at rest, orthopnea, tachypnea, paroxysmal nocturnal dyspnea, dizziness, confusion, cool extremities at rest, exercise intolerance, easy fatigueability, peripheral edema, nocturia, ascites, hepatomegaly, pulmonary edema, cyanosis, laterally displaced apex beat, gallop rhythm, heart murmurs, parasternal heave, and pleural effusion. In one embodiment the disorder is CHF; in another embodiment the disorder is DCM. In another embodiment, the disorder is ischemia without heart failure. While not being bound by any mechanism of action, the inventors believe that current failure of cell therapy efforts to treat disorders such as CHF (based at least in part on the lack of survival of implanted stem cells) is related to trying to grow cells in a hostile environment without adequate blood supply/matrix support. Without adequate extracellular matrix, injected cells clump due to lack of physical support for the cells to attach. In contrast, co-populating the 3DFC with cardiomyocytes and/or cardiac stem cells as per the methods of the present invention will enable these cells to grow and engraft onto the heart. This coupled with improved blood flow will result in more viable myocardium to treat the disorders disclosed above, for example, through improved left ventricular (LV) function and reduced maladaptive LV remodeling. The 3DFC provides growth factor stimulation to enhance matrix support/new blood vessel formation allowing cardiomyocytes and/or cardiac stem cells to engraft and grow. Fibroblasts in the 3DFC produce angiogenic growth factors: VEGF (vascular endothelial growth factor), HGF (hepatocyte growth factor), bFGF (basic fibroblast growth factor), and angiopoietin-1 (See, for example, J. Anat. (2006) 209, pp 527-532), which also help to provide vasculature for survival of the seeded cardiomyocytes. Thus, a significant advantage of the co-culture on 3DFC is that the 3DFC is pro-angiogenic or pro-arteriogenic, and thus addresses ischemia at the same time the co-cultured patch is delivering cells or beating function to the heart. Thus, the underlying 3DFC makes the ischemic myocardium more friendly to the seeded cells and thus more likely to survive and become functional, which can include migrating off the construct to functionally integrate into the myocardium, or remaining on the construct. As will be clear to those of skill in the art, the construct also can be used as an adjunct therapy, to provide a pumping assist without integration of the cardiomyocytes into the heart myocardium.

Thus, in a further alternative embodiment that can be combined with any other embodiment herein, the construct is a seeded, non-contracting 3DFC patch to provide cardiomyocytes to the host heart and to become functional or to functionally integrate into the myocardium. In another alternative embodiment that can be combined with any other embodiment herein, the construct is a contractile construct and may be used, for example, as an adjunct therapy, to provide a pumping assist without integration of the cardiomyocytes into the heart myocardium.

In the methods of the invention, attaching the matrix scaffold to the heart subjects it to mechanical stress that stimulates cell migration, growth, and secretion of extracellular matrix protein. The rhythmic stretching of the scaffold facilitates nutrient and waste exchange within the scaffold by opening and compressing the scaffold pores.

Thus, the present methods utilize the 3DFC as a delivery system for cell-based therapy using the heart as its own bioreactor to support the engraftment/growth of cells seeded on the 3DFC. The methods of the invention permit covering a larger amount of myocardium as opposed to isolated cell injections, thus addressing one criticism as to why cell injections appear to work better in rodents than humans, ie., the amount of damaged myocardium needed to treat. Also cells seeded on the 3DFC will not wash out in the circulation as seen with insolated cell injections.

In an alternative embodiment that can be combined with any other embodiments herein, the subject is a mammal, most preferably a human. In a further alternative embodiment that can be combined with any other embodiments herein, the subject is human. In another alternative embodiment, the cardiomyocytes or cardiac stem cells are obtained from the subject.

As used herein, "CHF" is a chronic (as opposed to rapid onset) impairment of the heart's ability to supply adequate blood to meet the body's needs. CHF may be caused by, but is distinct from, cardiac arrest, myocardial infarction, and cardiomyopathy. In one alternative embodiment, the subject suffers from congestive heart failure. In various further alternative embodiments that can be combined with any other embodiments herein, the subject's heart failure comprises left heart failure, right heart failure, backward heart failure (increased venous back pressure), forward heart failure (failure to supply adequate arterial perfusion), systolic dysfunction, diastolic dysfunction, systemic vascular resistance, low-output heart failure, high-output heart failure. In various further alternative embodiments that can be combined with any other embodiments herein, the subject's CHF may be any of Classes I-IV as per the New York Heart Association Functional Classification; more preferably Class III or IV.

Class I: no limitation is experienced in any activities; there are no symptoms from ordinary activities.

Class II: slight, mild limitation of activity; the patient is comfortable at rest or with mild exertion.

Class III: marked limitation of any activity; the patient is comfortable only at rest.

Class IV: any physical activity brings on discomfort and symptoms occur at rest.

In a further alternative embodiment that can be combined with any other embodiments herein, the subject has been diagnosed with CHF according to the New York Heart Association Functional Classification. In a further alternative embodiment that can be combined with any other embodiments herein, the subject is further characterized by one or more of the following: hypertension, obesity, cigarette smoking, diabetes, valvular heart disease, and ischemic heart disease.

As used herein, "treat" or "treating" means accomplishing one or more of the following: (a) reducing the severity of the disorder (ex: treatment of Class IV subject to improve status to Class III for CHF subjects); (b) limiting or preventing development of symptoms characteristic of the disorder; (c) inhibiting worsening of symptoms characteristic of the disorder; (d) limiting or preventing recurrence of symptoms in patients that were previously symptomatic for the disorder. Signs characteristic of CHF include, but are not limited to reduced ejection fraction, reduced myocardial perfusion, maladaptive cardiac remodeling (such as left ventricle remodeling), reduced left ventricle function, dyspnea on exertion, dyspnea at rest, orthopnea, tachypnea, paroxysmal nocturnal dyspnea, dizziness, confusion, cool extremities at rest, exercise intolerance, easy fatigueability, peripheral edema, nocturia, ascites, hepatomegaly, pulmonary edema, cyanosis, laterally displaced apex beat, gallop rhythm, heart murmurs, parasternal heave, and pleural effusion.

In one embodiment, the constructs described herein find use in promoting the healing of ischemic heart tissue. The ability of the constructs to promote the healing of an ischemic tissue depends in part, on the severity of the ischemia. As will be appreciated by the skilled artisan, the severity of the ischemia depends, in part, on the length of time the tissue has been deprived of oxygen. Among such activities is the reduction or prevention of the remodeling of ischemic tissue. By "remodeling" herein is meant, the presence of one or more of the following: (1) a progressive thinning of the ischemic tissue, (2) a decrease in the number or blood vessels supplying the ischemic tissue, and/or (3) a blockage in one or more of the blood vessels supplying the ischemic tissue, and if the ischemic tissue comprises muscle tissue, (4) a decrease in the contractibility of the muscle tissue. Untreated, remodeling typically results in a weakening of the ischemic tissue such that it can no longer perform at the same level as the corresponding healthy tissue. Cardiovascular ischemia is generally a direct consequence of coronary artery disease, and is usually caused by rupture of an atherosclerotic plaque in a coronary artery, leading to formation of thrombus, which can occlude or obstruct a coronary artery, thereby depriving the downstream heart muscle of oxygen. Prolonged ischemia can lead to cell death or necrosis, and the region of dead tissue is commonly called an infarct.

In some embodiments, candidate subjects for the methods described herein will be patients with stable angina and reversible myocardial ischemia. Stable angina is characterized by constricting chest pain that occurs upon exertion or stress, and is relieved by rest or sublingual nitroglycerin. Coronary angiography of patients with stable angina usually reveals 50-70% obstruction of at least one coronary artery. Stable angina is usually diagnosed by the evaluation of clinical symptoms and ECG changes. Patients with stable angina may have transient ST segment abnormalities, but the sensitivity and specificity of these changes associated with stable angina are low.

In some embodiments, candidates for the methods described herein will be patients with unstable angina and reversible myocardial ischemia. Unstable angina is characterized by constricting chest pain at rest that is relieved by sublingual nitroglycerin. Anginal chest pain is usually relieved by sublingual nitroglycerin, and the pain usually subsides within 30 minutes. There are three classes of unstable angina severity: class I, characterized as new onset, severe, or accelerated angina; class II, subacute angina at rest characterized by increasing severity, duration, or requirement for nitroglycerin; and class III, characterized as acute angina at rest. Unstable angina represents the clinical state between stable angina and acute myocardial infarction (AMI) and is thought to be primarily due to the progression in the severity and extent of atherosclerosis, coronary artery spasm, or hemorrhage into non-occluding plaques with subsequent thrombotic occlusion. Coronary angiography of patients with unstable angina usually reveals 90% or greater obstruction of at least one coronary artery, resulting in an inability of oxygen supply to meet even baseline myocardial oxygen demand. Slow growth of stable atherosclerotic plaques or rupture of unstable atherosclerotic plaques with subsequent thrombus formation can cause unstable angina. Both of these causes result in critical narrowing of the coronary artery. Unstable angina is usually associated with atherosclerotic plaque rupture, platelet activation, and thrombus formation. Unstable angina is usually diagnosed by clinical symptoms, ECG changes, and changes in cardiac markers.

In some embodiments, candidates for the methods described herein will be human patients with left ventricular dysfunction and reversible myocardial ischemia that are undergoing a coronary artery bypass graft (CABG) procedure, who have at least one graftable coronary vessel and at least one coronary vessel not amenable to bypass or percutaneous coronary intervention.

In some embodiments, application of the construct to an ischemic tissue increases the number of blood vessels present in the ischemic tissue, as measured using laser Doppler imaging (see, e.g., Newton et al., 2002, J Foot Ankle Surg, 41(4):233-7). In some embodiments, the number of blood vessels increases 1%, 2%, 5%; in other embodiments, the number of blood vessels increases 10%, 15%, 20%, even as much as 25%, 30%, 40%, 50%; in some embodiments, the number of blood vessels increase even more, with intermediate values permissible.

In some embodiments, application of the construct to an ischemic heart tissue increases the ejection fraction. In a healthy heart, the ejection fraction is about 65 to 95 percent. In a heart comprising ischemic tissue, the ejection fraction is, in some embodiments, about 20-40 percent. Accordingly, in some embodiments, treatment with the construct results in a 0.5 to 1 percent absolute improvement in the ejection fraction as compared to the ejection fraction prior to treatment. In other embodiments, treatment with the construct results in an absolute improvement in the ejection fraction more than 1 percent. In some embodiments, treatment results in an absolute improvement in the ejection fraction of 1.5%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, or more as compared to the ejection fraction prior to treatment. For example, if the ejection fraction prior to treatment was 40%, then following treatment ejection fractions between 41% to 59% or more are observed in these embodiments. In still other embodiments, treatment with the construct results in an improvement in the ejection fraction greater than 10% as compared to the ejection fraction prior to treatment.

In some embodiments, application of the construct to an ischemic heart tissue increases one or more of cardiac output (CO) (increases of up to 55% or more relative to pre-status treatment), left ventricular end diastolic volume index (LVEDVI), left ventricular end systolic volume index (LVESVI), and systolic wall thickening (SWT). These parameters are measured by art-standard clinical procedures, including, for example, nuclear scans, such as radionuclide ventriculography (RNV) or multiple gated acquisition (MUGA), and X-rays.

In some embodiments, application of the construct to an ischemic heart tissue causes a demonstrable improvement in the blood level of one or more protein markers used clinically as indicia of heart injury, such as creatine kinase (CK), serum glutamic oxalacetic transaminase (SGOT), lactic dehydrogenase (LDH) (see, e.g., U.S. Publication 2005/0142613), troponin I and troponin T can be used to diagnose heart muscle injury (see, e.g., U.S. Publication 2005/0021234). In yet other embodiments, alterations affecting the N-terminus of albumin can be measured (see, e.g., U.S. Publications 2005/0142613, 2005/0021234, and 2005/0004485; the disclosures of which are incorporated herein by reference in their entireties).

Additionally, the cultured three-dimensional tissue can be used with therapeutic devices used to treat heart disease including heart pumps, endovascular stents, endovascular stent grafts, left ventricular assist devices (LVADs), biventricular cardiac pacemakers, artificial hearts, and enhanced external counterpulsation (EECP).

In a further alternative embodiment that can be combined with any other embodiments herein, the treating results in production of new cardiomyocytes and new blood vessels in the subject. In a further alternative embodiment that can be combined with any other embodiments herein, the treating results in improvement of left ventricular function, fall in end diastolic pressure (EDP) (reduction of up to 50-60% or more relative to pre-status treatment), myocardial perfusion, repopulation of the anterior wall with cardiomyocytes, and/or reversing maladaptive left ventricle remodeling in the subject.

In one non-limiting alternative embodiment in which a synchronously beating construct is placed on the heart to aid in contraction of the left ventricle, beneficial treatment can be demonstrated by an improvement in ejection fraction. In a further non-limiting alternative embodiment, a non-beating construct is placed on the heart, then spontaneously begins beating on the heart to aid in contraction of the heart.

The construct can be contacted with the heart in any suitable way to promote attachment. The construct may be attached to various locations on the heart, including the epicardium, myocardium and endocardium, most preferably the epicardium. Means for attachment include, but are not limited to, direct adherence between the construct and the heart tissue, biological glue, suture, synthetic glue, laser dyes, or hydrogel. A number of commercially available hemostatic agents and sealants include SURGICAL® (oxidized cellulose), ACTIFOAM® (collagen), FIBRX® (light-activated fibrin sealant), BOHEAL® (fibrin sealant), FIBROCAPS® (dry powder fibrin sealant), polysaccharide polymers p-GlcNAc (SYVEC® patch; Marine Polymer Technologies), Polymer 27CK (Protein Polymer Tech.). Medical devices and apparatus for preparing autologous fibrin sealants from 120 ml of a patient's blood in the operating room in one and one-half hour are also known (e.g. Vivostat System).

In an alternative embodiment of the invention utilizing direct adherence, the construct is placed directly onto the heart and the product attaches via natural cellular attachment. In a further alternative embodiment, the construct is attached to the heart using surgical glue, preferably biological glue such as a fibrin glue. The use of fibrin glue as a surgical adhesive is well known. Fibrin glue compositions are known (e.g., see U.S. Pat. Nos. 4,414,971; 4,627,879 and 5,290,552) and the derived fibrin may be autologous (e.g., see U.S. Pat. No. 5,643,192). The glue compositions may also include additional components, such as liposomes containing one or more agent or drug (e.g., see U.S. Pat. Nos. 4,359,049 and 5,605,541) and include via injection (e.g., see U.S. Pat. No. 4,874,368) or by spraying (e.g., see U.S. Pat. Nos. 5,368,563 and 5,759,171). Kits are also available for applying fibrin glue compositions (e.g., see U.S. Pat. No. 5,318,524).

In another embodiment, a laser dye is applied to the heart, the construct, or both, and activated using a laser of the appropriate wavelength to adhere to the tissues. In alternative embodiments, the laser dye has an activation frequency in a range that does not alter tissue function or integrity. For instance, 800 nm light passes through tissues and red blood cells. Using indocyan green (ICG) as the laser dye, laser wavelengths that pass through tissue may be used. A solution of 5 mg/ml of ICG is painted onto the surface of the three-dimensional stromal tissue (or target site) and the ICG binds to the collagen of the tissue. A 5 ms pulse from a laser emitting light with a peak intensity near 800 nm is used to activate the laser dye, resulting in the denaturation of collagen which fuses elastin of the adjacent tissue to the modified surface.

In another embodiment, the construct is attached to the heart using a hydrogel. A number of natural and synthetic polymeric materials are sufficient for forming suitable hydrogel compositions. For example, polysaccharides, e.g., alginate, may be crosslinked with divalent cations, polyphosphazenes and polyacrylates are crosslinked ionically or by ultraviolet polymerization (U.S. Pat. No. 5,709,854). Alternatively, a synthetic surgical glue such as 2-octyl cyanoacrylate ("DERMABOND", Ethicon, Inc., Somerville, N.J.) may be used to attach the three-dimensional stromal tissue.

In an alternative embodiment of the present invention, the construct is secured to the heart using one or more sutures, including, but not limited to, 5-O, 6-O and 7-O proline sutures (Ethicon Cat. Nos. 8713H, 8714H and 8701H), poliglecaprone, polydioxanone, polyglactin or other suitable non-biodegradable or biodegradable suture material. When suturing, double armed needles are typically, although not necessarily, used.

In another embodiment, the 3DFC is grown in a bioreactor system (e.g., U.S. Pat. Nos. 5,763,267 and 5,843,766) in which the framework is slightly larger than the final tissue-engineered product. The final product contains a border, one edge, flap or tab of the scaffold material, which is used as the site for application of the biological/synthetic glue, laser dye or hydrogel. In alternative embodiments, the scaffold weave may be used as an attachment for suturing or microsuturing.

As used herein, the phrase "an amount effective" means an amount of the construct that will be effective to treat the disorder, as discussed herein. As will be clear to those of skill in the art, the methods comprise the use of one or more of the recited constructs to treat disorders characterized by a lack of functioning cardiomyocytes. In one embodiment, the method comprises contacting the heart with an amount of one or more constructs that serves to cover one or more ischemic regions of the heart, preferably all ischemic regions of the heart. The construct is used in an amount effective to promote tissue healing and/or revascularization of weakened or damaged heart tissue in an individual diagnosed with a disorder characterized by a lack of functioning cardiomyocytes. The amount of the construct administered, depends, in part, on the severity of the disorder, whether the construct is used as an injectable composition (see, US20060154365, incorporated herein by reference in its entirety), the concentration of the various growth factors and/or Wnt proteins present, the number of viable cells comprising the construct, and/or ease of access to the heart tissue(s) being treated. Determination of an effective dosage is well within the capabilities of those skilled in the art. Suitable animal models, such as the canine model described in US 20060292125 (incorporated by reference herein in its entirety) can be used for testing the efficacy of the dosage on a particular tissue of the heart.

As used herein "dose" refers to the number of cohesive pieces of construct applied to the heart of an individual diagnosed with congestive heart failure. A typical cohesive piece of construct is approximately 35 cm$^2$. As will be appreciated by those skilled in the art, the absolute dimensions of the cohesive piece can vary, as long it comprises a sufficient number of cells to promote healing of weakened or damaged heart tissue in an individual diagnosed with a disorder characterized by a lack of functioning cardiomyocytes. Thus, cohesive pieces suitable for use in the methods described herein can range in size from 15 cm$^2$ to 50 cm$^2$.

The application of more than one cohesive piece of construct can be used to increase the area of the heart treatable by the methods described herein. For example, in embodiments using a two pieces of cohesive construct, the treatable area is approximately doubled in size. In embodiments using three cohesive pieces of construct, the treatable area is approximately tripled in size. In embodiments using four cohesive pieces of construct, the treatable area is approximately quadrupled in size. In embodiments using five cohesive pieces of construct, the treatable area is approximately five-fold, i.e. from 35 cm$^2$ to 175 cm$^2$.

In some embodiments, one cohesive piece of construct is attached to a region of the heart in an individual diagnosed with a disorder characterized by a lack of functioning cardiomyocytes.

In other embodiments, two cohesive pieces of construct are attached to a region of the heart in an individual diagnosed with a disorder characterized by a lack of functioning cardiomyocytes.

In other embodiments, three cohesive pieces of construct are attached to a region of the heart in an individual diagnosed with a disorder characterized by a lack of functioning cardiomyocytes.

In other embodiments, four, five, or more cohesive pieces of construct are attached to a region of the heart in an individual diagnosed with a disorder characterized by a lack of functioning cardiomyocytes.

In embodiments in which two or more cohesive pieces of construct are administered, the proximity of one piece to another can be adjusted, depending in part on, the severity of the disorder characterized by a lack of functioning cardiomyocytes, the extent of the area being treated, and/or ease of access to the heart tissue(s) being treated. For example, in some embodiments, the pieces of 3DFC can be located immediately adjacent to each other, such that one or more edges of one piece contact one or more edges of a second piece. In other embodiments, the pieces can be attached to the heart tissue such that the edges of one piece do not touch the edges of another piece. In these embodiments, the pieces can be separated from each other by an appropriate distance based on the anatomical and/or disease conditions presented by the subject. Determination of the proximity of one piece to another, is well within the capabilities of those skilled in the art, and if desired can be tested using suitable animal models, such as the canine model described in US20060292125.

In embodiments that comprise a plurality of pieces of construct, some, or all of the pieces can be attached to the same or different areas of the heart.

In embodiments that comprise a plurality of pieces of construct, the pieces are simultaneously attached, or concurrently attached to the heart.

In some embodiments, the construct pieces are administered over time. The frequency and interval of administration depends, in part, on the severity of the disorder, whether the 3DFC is used as an injectable composition (see, US20060154365, incorporated herein by reference in its entirety), the concentration of the various growth factors and/or Wnt proteins present, the number of viable cells comprising the 3DFC, and/or ease of access to the heart tissue(s) being treated. Determination of the frequency of administration and the duration between successive applications is well within the capabilities of those skilled in the art, and if desired, can be tested using suitable animal models, such as the canine model described in US20060292125.

In a further alternative embodiment, one or more construct is contacted with the left ventricle. In a further alternative embodiment, the one or more constructs cover the entire heart.

In embodiments that comprise a plurality of pieces of construct, some, or all of the pieces can be attached to the area comprising the heart. In other embodiments, one or more of the construct pieces can be attached to areas that do not comprise damaged myocardium. For example, in some embodiments, one piece can be attached to an area comprising ischemic tissue and a second piece can be attached to an adjacent area that does not comprise ischemic tissue. In these embodiments, the adjacent area can comprise damaged or defective tissue. "Damaged," or "defective" tissue as used herein refer to abnormal conditions in a tissue that can be caused by internal and/or external events, including, but not limited to, the event that initiated the ischemic tissue. Other events that can result in ischemic, damaged or defective tissue include disease, surgery, environmental exposure, injury, aging, and/or combinations thereof.

In embodiments that comprise a plurality of pieces of cultured three-dimensional tissue, the construct pieces can be simultaneously attached, or concurrently attached to an ischemic tissue.

In an alternative embodiment that can be combined with any other embodiment disclosed herein, the cardiomyocytes or precursors thereof are adhered to the 3DFC at a cell density ranging between $0.5 \times 10^6$ cells/cm$^2$ and $5 \times 10^6$ cells/cm$^2$; more preferably between $1 \times 10^6$ cells/cm$^2$ and $4 \times 10^6$ cells/cm$^2$; and most preferably between $1.5 \times 10^6$ cells/cm$^2$ and $3 \times 10^6$ cells/cm$^2$. In another embodiment that can be combined with any other embodiment disclosed herein, the cardiomyocytes or precursors thereof are seeded on the construct at a density between $1.5 \times 10^6$ cells/cm$^2$ and $3 \times 10^6$ cells/cm$^2$, and the fibroblasts are present on the construct at a density of between about $8.0 \times 10^5$ cells/cm$^2$ and about $2.0 \times 10^6$ cells/cm$^2$.

In various embodiments, the cardiomyocytes or precursors thereof are present in a ratio with fibroblasts on the construct of between about 1:10 and about 10:1; about 1:9 to about 9:1; about 1:8 to about 8:1; about 1:7 to about 7:1; about 1:6 to about 6:1; about 1:5 to about 5:1; about 1:4 to about 4:1; about 1:3 to about 3:1; about 1:2 to about 2:1; or about 1:1. Other ratios of cells are also possible.

In a further alternative embodiment that can be combined with any other embodiment herein, the cardiomyocytes or precursors thereof are engineered to express a therapeutic of interest, such as thymosin beta-4 (TB4), akt murine thyoma viral oncogene homolog (AKT1), stroma cell-derived factor-1 alpha (SDF-1), and hepatocyte growth factor (HGF). Alternatively, one or more of thymosin beta-4 (TB4), akt murine thyoma viral oncogene homolog (AKT1), stroma cell-derived factor-1 alpha (SDF-1), and hepatocyte growth factor (HGF) can be added exogenously to the construct prior to implantation. (RegeneRx Biopharmaceuticals, Inc. (Bethesda, Md.) In this embodiment, the cardiomyocytes or precursors thereof will provide new cardiomyocytes to grow onto the damaged heart and the added factor(s) will augment cell migration and engraftment.

In various alternative embodiments, the cardiomyocytes or progenitors thereof are selected from the group consisting of cardiomyocytes, cardiac stem cells (such as c-kit+ cardiac stem cells, CD34+ endothelial progenitor cells, autologous bone marrow cells, and mesenchymal stem cells. In an alternative embodiment that can be combined with any other embodiment disclosed herein, the cardiomyocytes or precursors thereof are human cells, more preferably human cells derived from (ie, obtained from and possibly expanded ex vivo prior to administration) the subject to be treated (such as by standard biopsy or other surgical procedures).

The methods may further comprise systemic administration of cytokines to the subject, including but not limited to Insulin like growth factor (IGF), Hepatic Growth Factor (HGF), and Stromal cell-derived factor a (SDF-1a).

The methods and compositions described herein can be used in combination with conventional treatments, such as the administration of various pharmaceutical agents and surgical procedures. For example, in some embodiments, the cultured three-dimensional tissue is administered with one or more of the medications used to treat a disorder characterized by a lack of functioning cardiomyocytes. Medications suitable for use in the methods described herein include angiotensin-converting enzyme (ACE) inhibitors (e.g., enalapril, lisinopril, and captopril), angiotensin II (A-II) receptor blockers (e.g., losartan and valsartan), diuretics (e.g., bumetanide, furosemide, and spironolactone), digoxin, beta blockers, and nesiritide.

Additionally, the constructs can be used with other options used to treat a disorder characterized by a lack of functioning cardiomyocytes, including heart pumps, also referred to as left ventricular assist devices (LVADs), biventricular cardiac pacemakers, cardiac wrap surgery, artificial hearts, and enhanced external counterpulsation (EECP), and cardiac wrap surgery (see, e.g., U.S. Pat. Nos. 6,425,856, 6,085,754, 6,572,533, and 6,730,016, the contents of which are incorporated herein by reference).

In some embodiments, the construct is used in conjunction with cardiac wrap surgery. In these embodiments, a flexible pouch or jacket is used to deliver and/or attach the construct, which can be placed inside or embedded within the pouch prior to placement over the damaged or weakened heart tissue. In other embodiments, the pouch and the 3DFC can be joined together. For example, the pouch and the construct can be joined together using a stretchable stitch assembly. In other embodiments, the construct can be configured to comprise threads useful for joining the framework to the pouch. U.S. Pat. Nos. 6,416,459, 5,702,343, 6,077,218, 6,126,590, 6,155,972, 6,241,654, 6,425,856, 6,230,714, 6,241,654, 6,155,972, 6,293,906, 6,425,856, 6,085,754, 6,572,533, and 6,730,016 and U.S. Patent Publication Nos. 2003/0229265, and 2003/0229261, the contents of which are incorporated herein by reference, describe various embodiments of pouches and jackets, e.g., cardiac constraint devices, that can be used to deliver and/or attach the construct.

In some embodiments, other devices, in addition to the construct are attached to the pouch, e.g., electrodes for defibrillation, a tension indicator for indicating when the jacket is adjusted on the heart to a desired degree of tensioning, and used in the methods and compositions described herein. See, e.g., U.S. Pat. Nos. 6,169,922 and 6,174,279, the contents of which are incorporated herein by reference.

A number of methods can be used to measure changes in the functioning of the heart in subjects before and after attachment of the construct. For example, an echocardiogram can be used to determine the capacity at which the heart is pumping. The percentage of blood pumped out of the left ventricle with each heartbeat is referred to as the ejection fraction. In a healthy heart, the ejection fraction is about 60 percent. In an individual with chronic heart failure caused by the inability of the left ventricle to contract vigorously, i.e., systolic heart failure, the ejection fraction is usually less than 40 percent. Depending on the severity and cause of the heart failure, ejection fractions typically range from less than 40 percent to 15 percent or less. An echocardiogram can also be used to distinguish between systolic heart failure and diastolic heart failure, in which the pumping function is normal but the heart is stiff.

In some embodiments, echocardiograms are used to compare the ejection fractions before and following treatment with the construct. In certain embodiments, treatment with the construct results in improvements in the ejection fraction between 3 to 5 percent. In other embodiments, treatment with the construct results in improvements in the ejection fraction between 5 to 10 percent. In still other embodiments, treatment with the construct results in improvements in the ejection fraction greater than 10 percent.

Nuclear scans, such as radionuclide ventriculography (RNV) or multiple gated acquisition (MUGA) scanning can be used to determine how much blood the heart pumps with each beat. These tests are done using a small amount of dye injected in the veins of an individual A special camera is used to detect the radioactive material as it flows through the heart. Other tests include X-rays and blood tests. Chest X-rays can be used to determine the size of the heart and if fluid has accumulated in the lungs. Blood tests can be used to check for a specific indicator of congestive heart failure, brain natriuretic peptide (BNP). BNP is secreted by the heart in high levels when it is overworked. Thus, changes in the level of BNP in the blood can be used to monitor the efficacy of the treatment regime.

In a further aspect, the present invention provides kits for treating CHF, comprising a suitable construct as disclosed above and a means for attaching the construct to the heart or organ. The means for attachment may include any such attachment device as described above, for example, a composition of surgical glue, hydrogel, or preloaded prolene needles for microsuturing.

EXAMPLES

Example 1

3DFC Seeding and Co-Culture

The 3DFC patch is a cryopreserved human fibroblast-derived tissue composed of fibroblasts, extracellular matrix, and a bioabsorbable scaffold (21,22). The fibroblast cells were from a qualified cell bank; tested for animal viruses, retroviruses, cell morphology, karology, isoenzymes, and tumorgenicity, free from viruses, retroviruses, endotoxins and mycoplasma. The 3DFC was supplied frozen (5 cm×7.5 cm); it at −75°±10° C. until ready for use when it was placed in sterile PBS (34-37° C.) and applied to the heart within 60 minutes of removal.

Random Seeding: The 3DFC (ANGINERA™ obtained from and thawed per Theregen, Inc. protocols) was cut into near circular sections approximately 1.5 cm in diameter to fill the well space of a 24 well culture plate. After the 3DFC was placed in the bottom of the well and completely covering its base, 1.5 ml of media (10% FBS in DMEM-LG) containing $>3\times10^6$ enothelial progenitor cells (rat neonatal cardiomyocytes) were added in suspension over the 3DFC at 27° C. The plate containing the 3DFC and cellular suspension was then centrifuged at 1300 rpms for 5 min forcing the cells in suspension into the 3DFC at 27° C. The plate containing the 3DFC was then transferred to a cell incubator and incubated 24 hrs at 37° C. and 5% $CO_2$ to allow further cellular adhesion and proliferation (FIG. 1).

Adhesion of the desired cells onto the 3DFC was greatly enhanced when $>3\times10^8$ cells/ml are added in suspension. At this concentration there was a "traffic jam effect" that takes place causing all the cells in suspension to come in contact with the 3DFC at the same time thus clogging any openings in the 3DFC not allowing the added cells to pass thru.

Starting out with a large number of cells allowed all cells in suspension to migrate unto the 3DFC, the more cells that make contact with the 3DFC enabled some cells to pass through the pores ending up with 1.5 to 2 million cells seeded on the patch.

Figure 2:
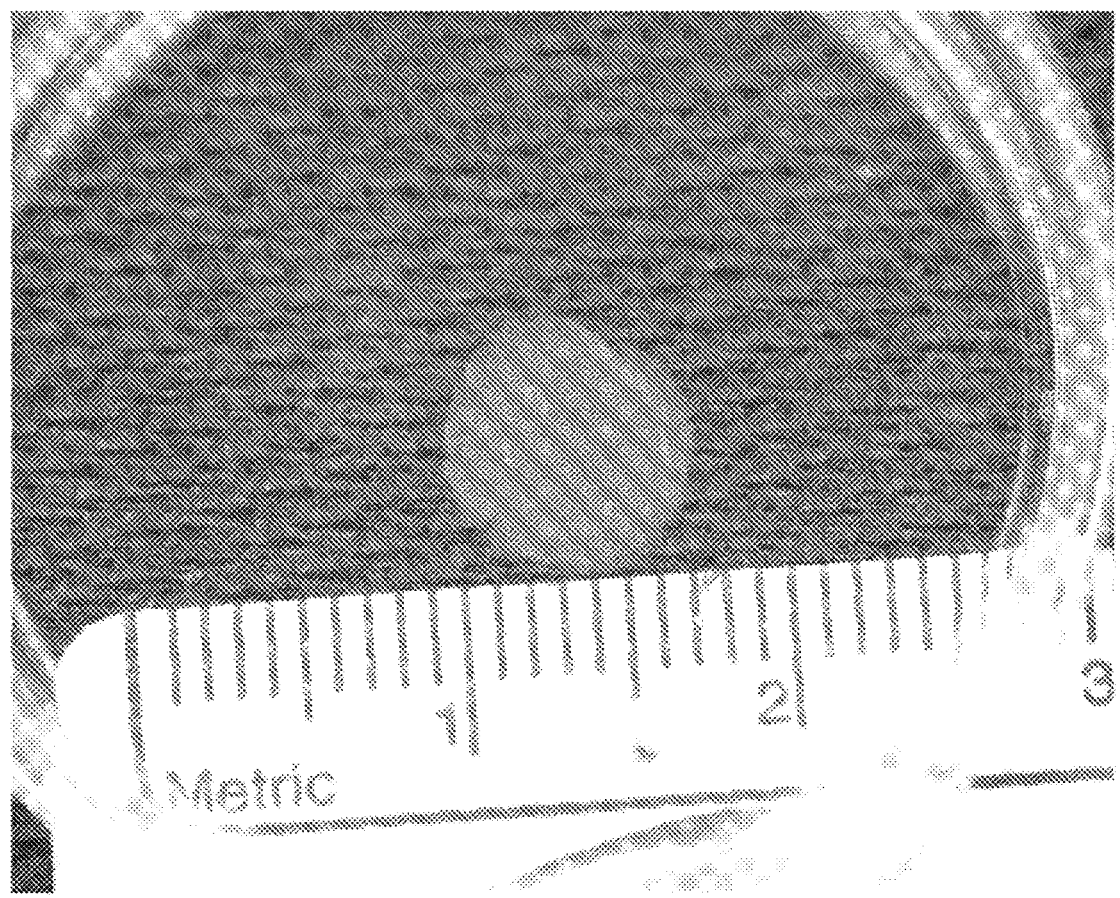
FIG. 2: Endothelial progenitor cells in a culture plate following isolation of an intact cell sheet. Cells maintain all cell-to-cell adhesion molecules and can be seeded and co-cultured onto the 3DFC.
Figure 3:
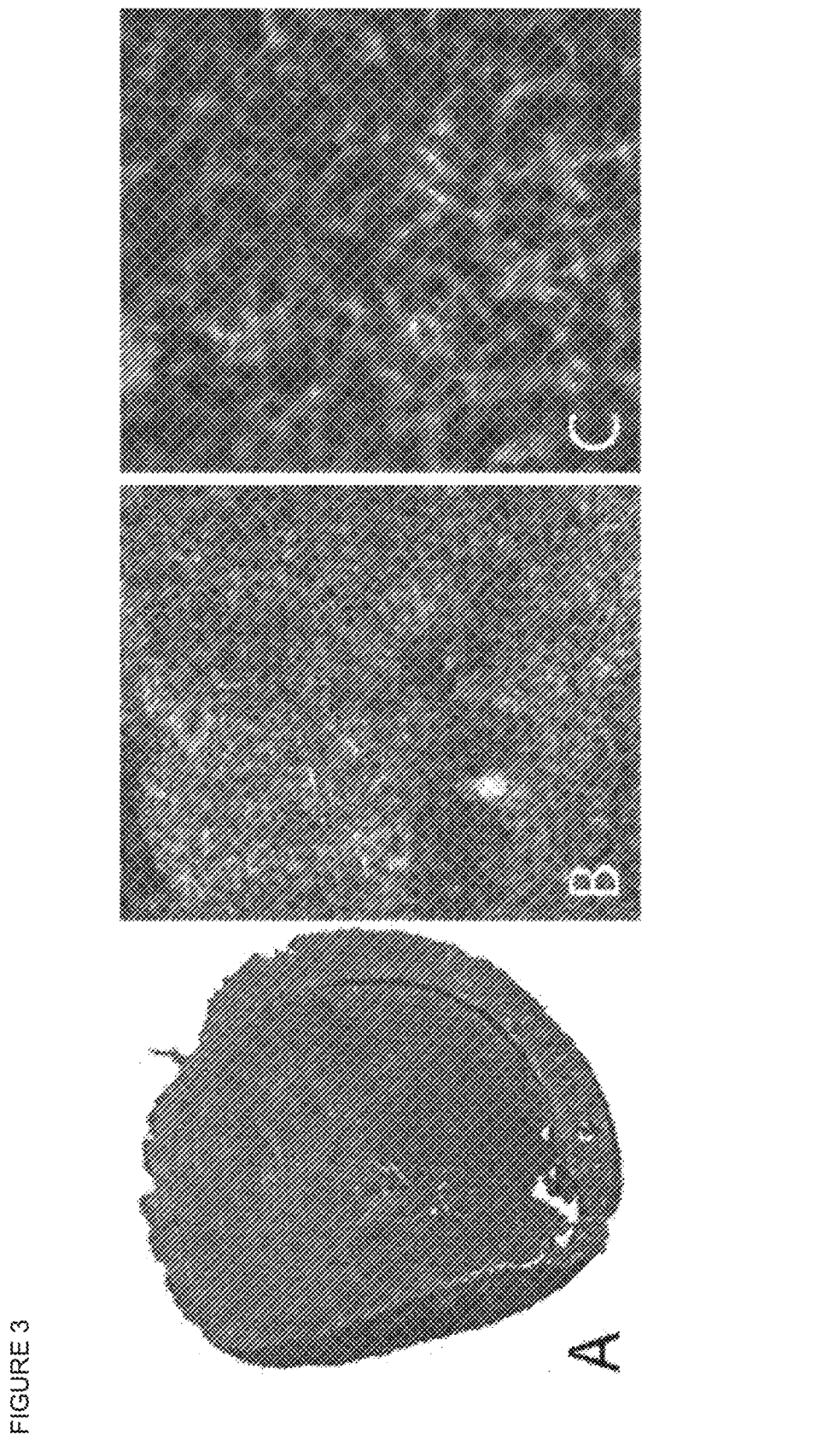
FIG. 3: Endothelial progenitor cell sheet after H&E stain. Dark purple represents nuclei while the lighter pink indicates cytoplasm. Image shows (A) the full cell sheet (~8 mm diameter) and (B&C) higher magnification.

Cell Sheet Seeding: Endothelial progenitor cells (bovine pulmonary arterial endothelial cells (BPAECS)) were grown in 24 well or 6 well culture plate (CellSeed, Japan) until they were confluent. The culture plates were then chilled to 20° C. allowing disassociation of the cell sheet from the culture plate. After 40 min the sheet was fully disassociated (FIGS. 2 & 3), and using a 5 ml, 10 ml, or 1000 ul pipette the disassociated cell sheet was taken up in existing culture media and transferred directly onto the 3DFC (obtained from and thawed per Theregen Inc. protocols).

Using 2-3 ul droplets of culture media dripped onto the new cell sheet (at 27° C.), the cell sheet unfolded to lay flat against the 3DFC. Once flat and flush against the 3DFC, the cell sheet+3DFC complex was incubated at 37° C. and 5% $CO_2$ for 10 min without additional media allowing for full adhesion of the cell sheet to the 3DFC. After, the seeded 3DFC was incubated over night prior to use (implantation, etc.).

Harvested cells sheets retained all cellular adhesion molecules and self-adhered when placed on the 3DFC. In addition, this method of cell harvesting kept intact all cell-to-cell interactions.

Example 2

Construction of a Spontaneously Contracting Biologically Active Cardiomyocyte Scaffold Methods: Cardiomyocytes were isolated from neonatal rats 1-2 days old and seeded onto 3DFC scaffolds that were cut into pieces of approximately 1.5-1.7 $cm^2$ in diameter. (ANGINERA™, obtained from Theregen, Inc) at concentrations ranging from $0.6\times10^6$ to $2.7\times10^6$ cells/$cm^2$. Briefly, the hearts were excised, atria removed and ventricles cut into 0.5-1 mm portions, minced, then digested in a pancreatin/collagenase solution. Following each enzymatic digest, cardiomyocytes were collected, combined and re-suspended in DMEM with 10% FBS. Lastly, the suspension was differentially plated in Ham's F-12 with 100 mg/ml BSA. The neonatal cardiomyocyte-3DFC were cultured between 1-10 days at 37° C. with 5% $CO_2$ in 10% FBS in DMEM-LG. Media was changed 24 hrs after initial plating then every 48 hrs.

Results: Higher density cardiomyocyte seedings ($1.8\times10^6$ to $2.7\times10^6$ cells/$cm^2$) of the 3DFC showed synchronized and spontaneous contractions of the entire scaffold after 48 hrs in culture. Contractions increased in robustness from 48 hrs to 5 days. Lower density cardiomyocyte seedings ($0.6$-$1.2\times10^6$ cells/$cm^2$) displayed non-synchronized yet spontaneous contractions. At 72 hours these contractions began synchronizing and by 84 hours, cell contractions were fully synchronized but contracted in a non-consistent manner. At 5 days, scaffolds seeded with $2.7\times10^6$ cells/$cm^2$ contracted in a consistent rhythmic and directional fashion (ie: medially, with each patch beating in a repetitive directional motion, squeezing "inwards"). Contractions were recorded at 71±3 beats BPM with a mean displacement of 2.9±0.1 mm and contraction velocity of 3.4±0.5 mm/sec (N=10).

Conclusion: These findings showed that isolated cardiomyocytes can be seeded and co-cultured onto a biodegradable 3-dimensional construct in a manner allowing cellular survival, communication and electrical coupling. These claims are supported by the observation that the newly seeded neonatal cardiomyocyte-3DFC scaffolds beat spontaneously and in a synchronized, directional fashion with no electrical stimulation. This newly formed neonatal cardiomyocyte 3DFC scaffold is a new and unique cell delivery system to treat CHF.

Example 3

Cellular Communications/Alignment

This example describes cardiomyocyte alignment on cardiomyocyte seeded 3DFC patches and in vivo improvements in rats with heart failure with treatment using the described cardiomyocyte seeded 3DFC (NCM-3DFC).

Connexin Formation: As shown above, isolated cardiomyocytes can be seeded and co-cultured onto the 3DFC; that these seeded patches contract spontaneously and rhythmically. In theory, rhythmic contractions support the hypothesis that the seeded cardiomyocytes align and establish complex connections with each other allowing for electromechanical cellular communication. These connections, known as connexins, are essential for the rhythmic contraction of cardiac muscle.

Figure 4:
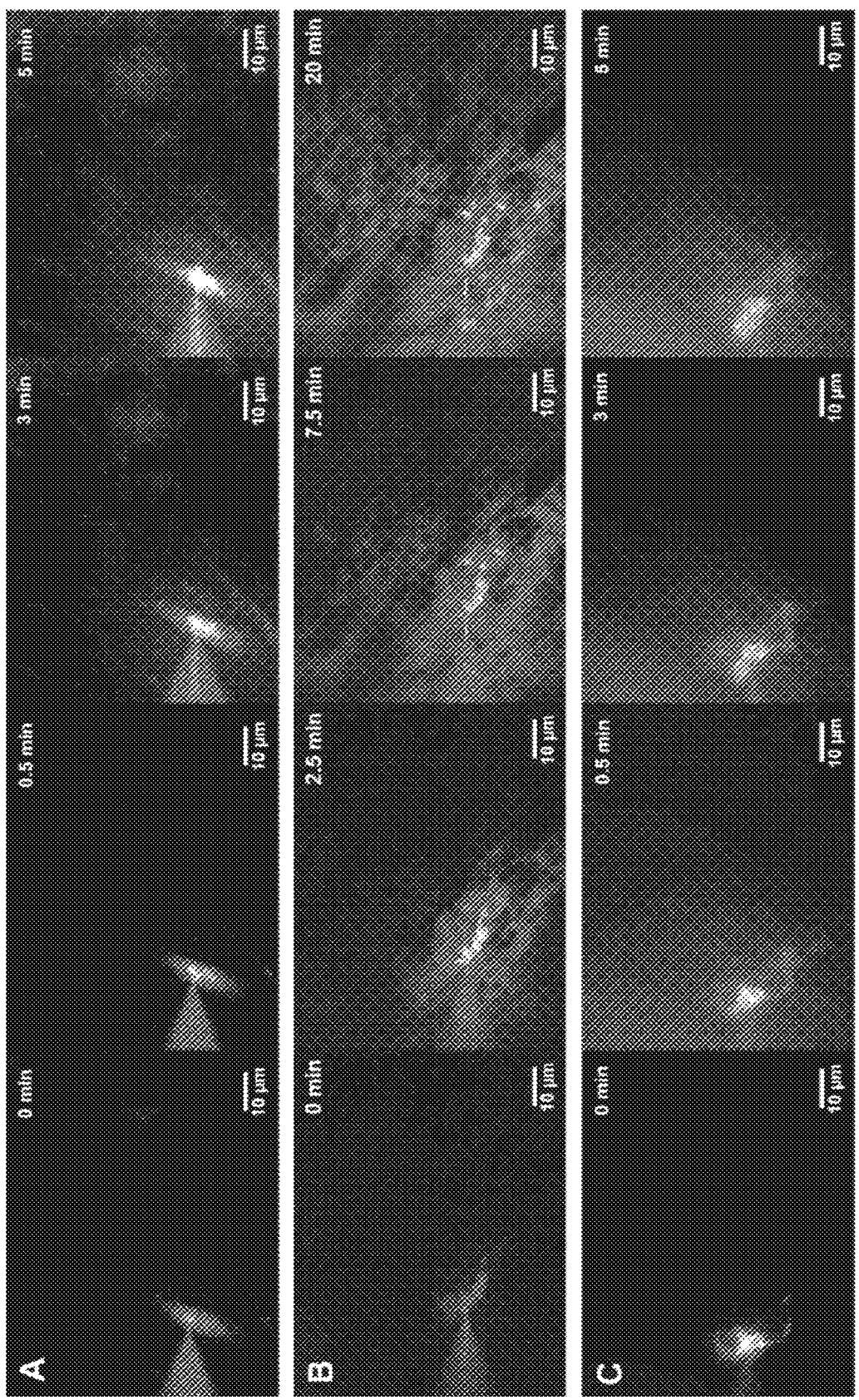
FIG. 4.

Cellular Injections: The following example shows connexin formation 24 hrs after cardiomycocyte seeding (same cell type as in example 2) and increased cellular connectiveness through connexin formation over time, up to 6 days, thus demonstrating connexin functionality within the 3DFC. In short, dye transfer was evaluated in both 3DFC and NCM-3DFC cultured for 6 days. Three dyes were injected simultaneously: [2-(4-nitro-2,1,3-benzoxadiol-7-yl)aminoethyl]trimethylammonium (NDB-TMA; mol wt 280, net charge 1+, 10 mM), Alexa 350 (mol wt 326, net charge 1−, 10 mM), and Rhodamine Dextran (0.1 mg/ml). Microelectrode tips were created from 1.0 mm filament glass (A-M Systems, Everett, Wash.) on a Sutter Instruments puller (Novato, Calif.). Tips were filled by capillary action with a mixture of the three dyes, backfilled with 200 mM KCl, and then lowered onto cell surface. Dye was slowly and continuously injected by capacitance overcompensation of the amplifier (A-M Systems). Photos were taken every 30 seconds (up to 2.5 min) then every 2.5 minutes up to 20 minutes. Cells that received dye from the injected cell after 10 minutes were compared between groups. Injections into cardiomyocyte seeded patches resulted in extensive dye passage between seeded cardiomyocytes (FIG. 4), demonstrating the functional presence of connexins. Non-seeded patches (fibroblasts only) resulted in retention of dye strictly in the primary cell, with no passage of dye into neighboring cells. Furthermore, addition of halothane, inhibited connexin activity as represented by disruption of dye transfer between cells (FIG. 4).

Histological Assessment: Additionally, histological assessment of cardiomyocyte seeded patches between 1, 4 and 8 days after seeding demonstrate that seeded cardiomyocytes adhere to the 3DFC and proceed to align on the surface of the 3DFC. The cardiomyocytes remain on the outer surface of the 3DFC, on the seeded face over time (one to eight days) and do not migrate into the 3DFC or to the opposite, non-seed side. (FIGS. 8-11) Cells centrifuged onto the patch were found to reside between the fibers of the 3DFC.

Figure 5:
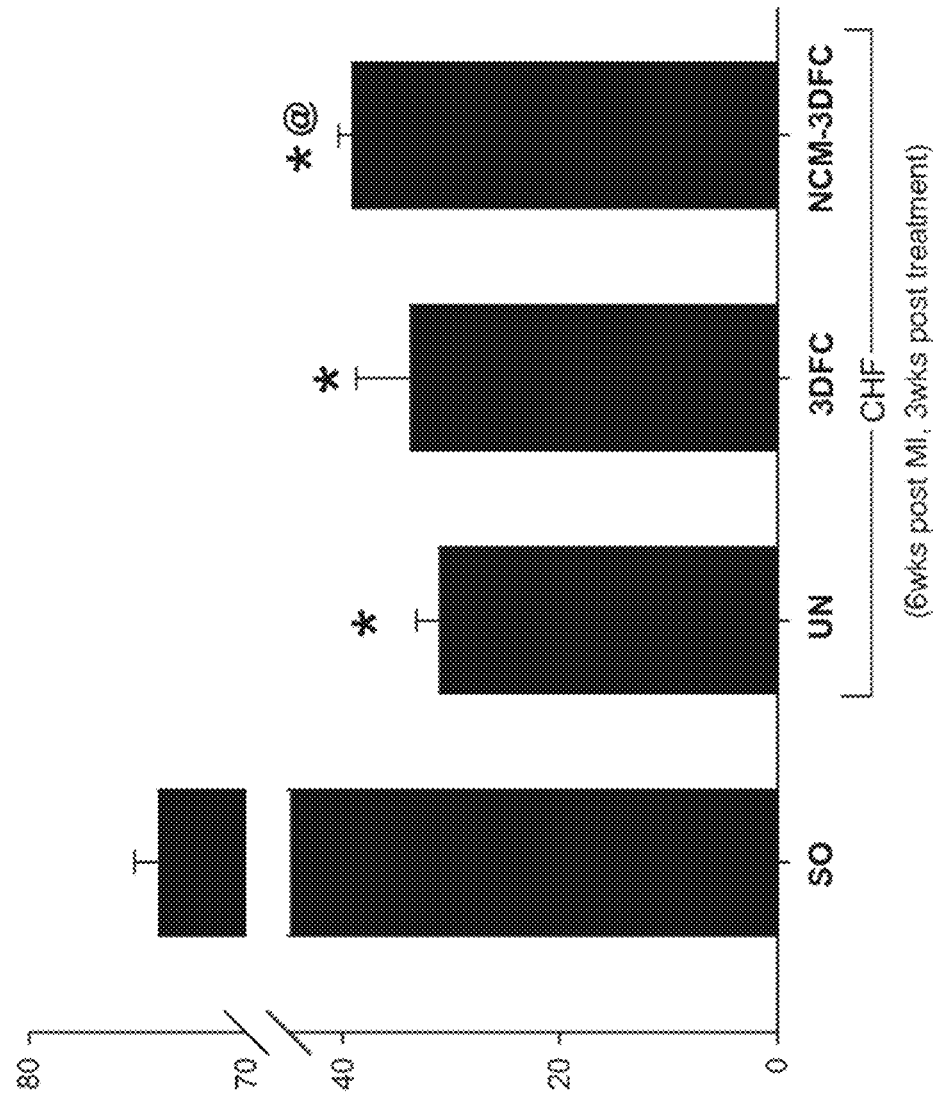
FIG. 5: Patches seeded with cardiomyocytes improved EF 25% in treated vs. sham rats after 3 wks. Data are mean±SE/. NCM-3DFC=Neonatal Cardiomyocyte 3DFC; SO=Sham Operated. SO, n=21; UN, n=12; 3DFC, n=9; NCM-3DFC, n=9. * P<0.05 vs SO; @P<0.05 vs UN; # P<0.05 vs 3DFC.
Figure 6:
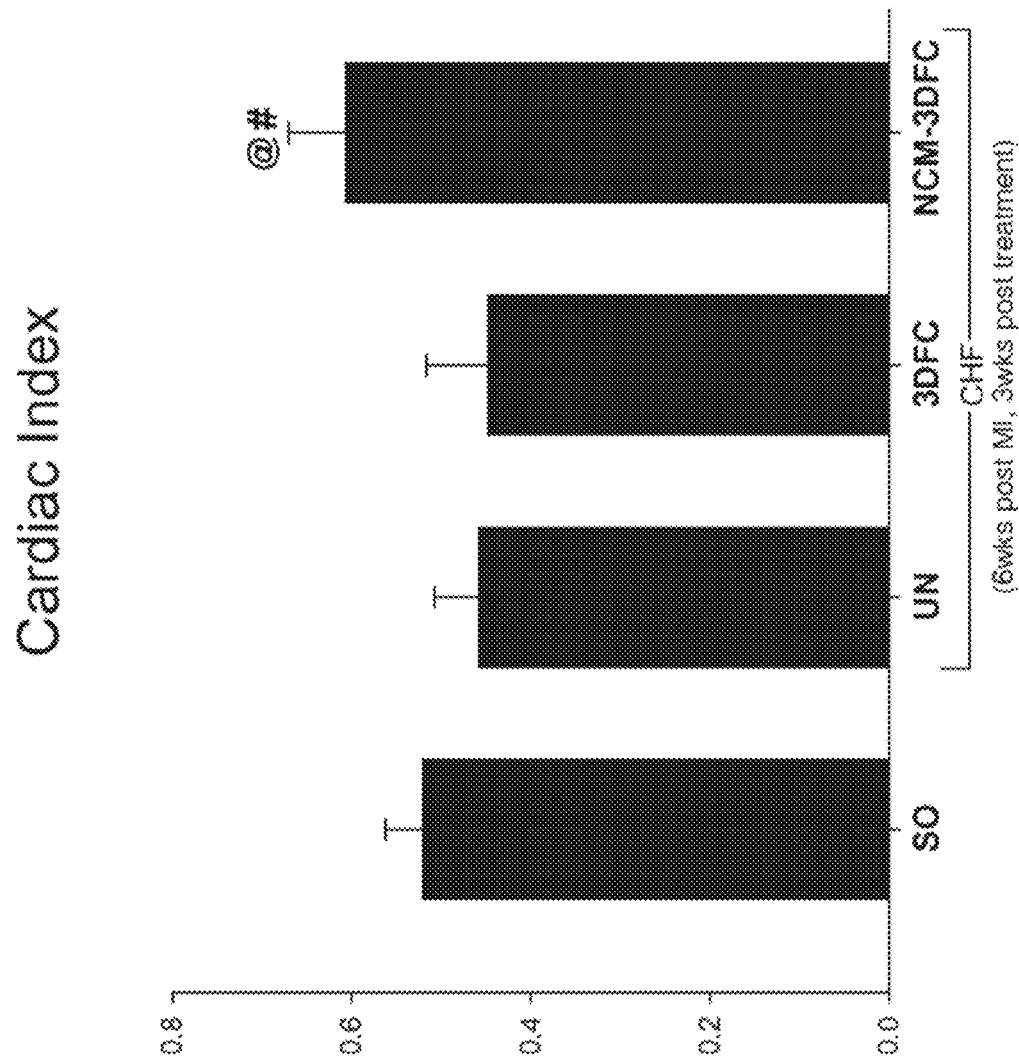
FIG. 6: Patches seeded with cardiomyocytes improved cardiac index (ml/(min X grams)) 55% in treated vs. sham rats after 3 wks. Data are mean±SE. NCM-3DFC=Neonatal Cardiomyocyte 3DFC; SO=Sham Operated. SO, n=21; UN, n=12; 3DFC, n=9; NCM-3DFC, n=9. * P<0.05 vs SO; @ P<0.05 vs UN; # P<0.05 vs 3DFC.
Figure 7:
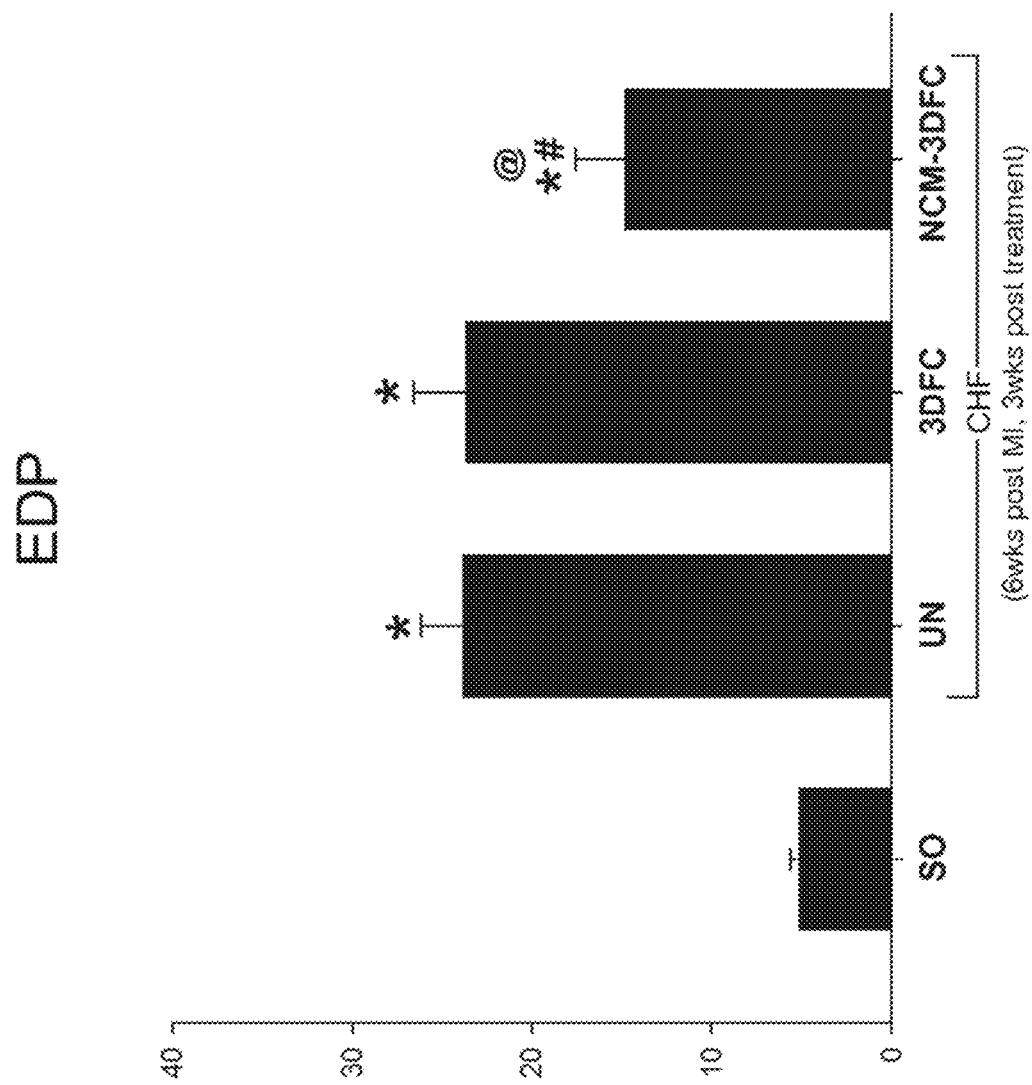
FIG. 7: Patches seeded with cardiomyocytes improved end diastolic pressure (mmHg) in treated vs. sham rats after 3 wks. Data are mean±SE. NCM-3DFC=Neonatal Cardiomyocyte 3DFC; SO=Sham Operated. SO, n=19; UN (untreated), n=12; 3DFC, n=9; NCM-3DFC, n=9. * P<0.05 vs SO; @ P<0.05 vs UN; # P<0.05 vs 3DFC.
Figure 8:
FIG. 8: Hematoxylin and eosin stained 3DFC (A) and cardiomyocyte seeded 3DFC (B & C). 10× magnification of 3DFC (A) orientated horizontally. Vicryl bundles (in purple) and fibroblasts nuclei blue/purple dots. 5× magnification of cardiomyocyte seeded 3DFC (B) orientated horizontally. 10× magnification of cardiomyocyte seeded 3DFC (C) orientated horizontally. The large cellular bundles (B & C) consist of cardiomyocytes situated between vicryl fibers.
Figure 9:
FIG. 9: 10× magnification H&E of 3DFC orientated horizontally. Vicryl bundles (in purple) and fibroblasts nuclei blue/purple dots.
Figure 10:
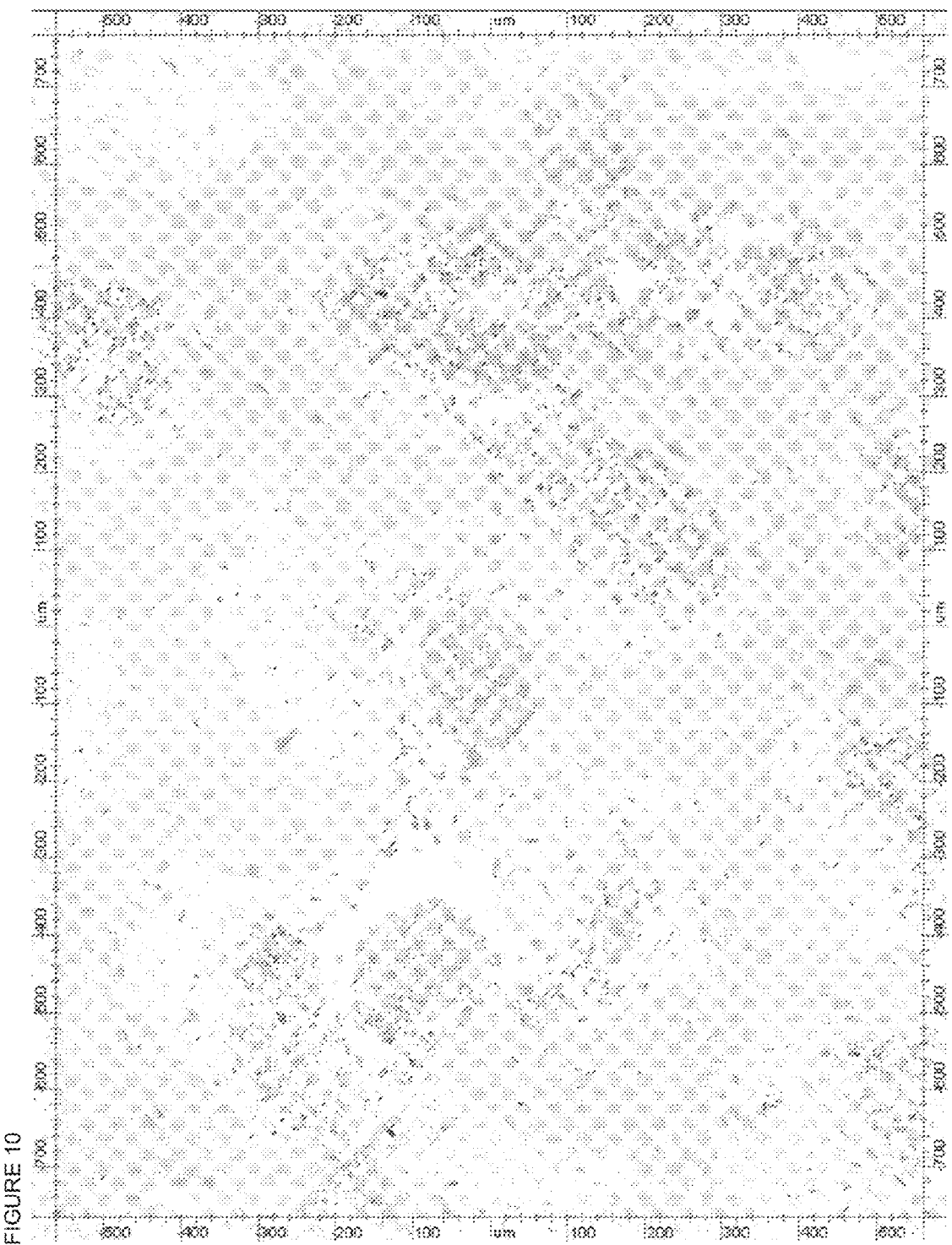
FIG. 10: 5× magnification H&E of cardiomyocyte seeded 3DFC orientated horizontally. The large cellular bundles consist of cardiomyocytes situated between vicryl fibers.
Figure 11:
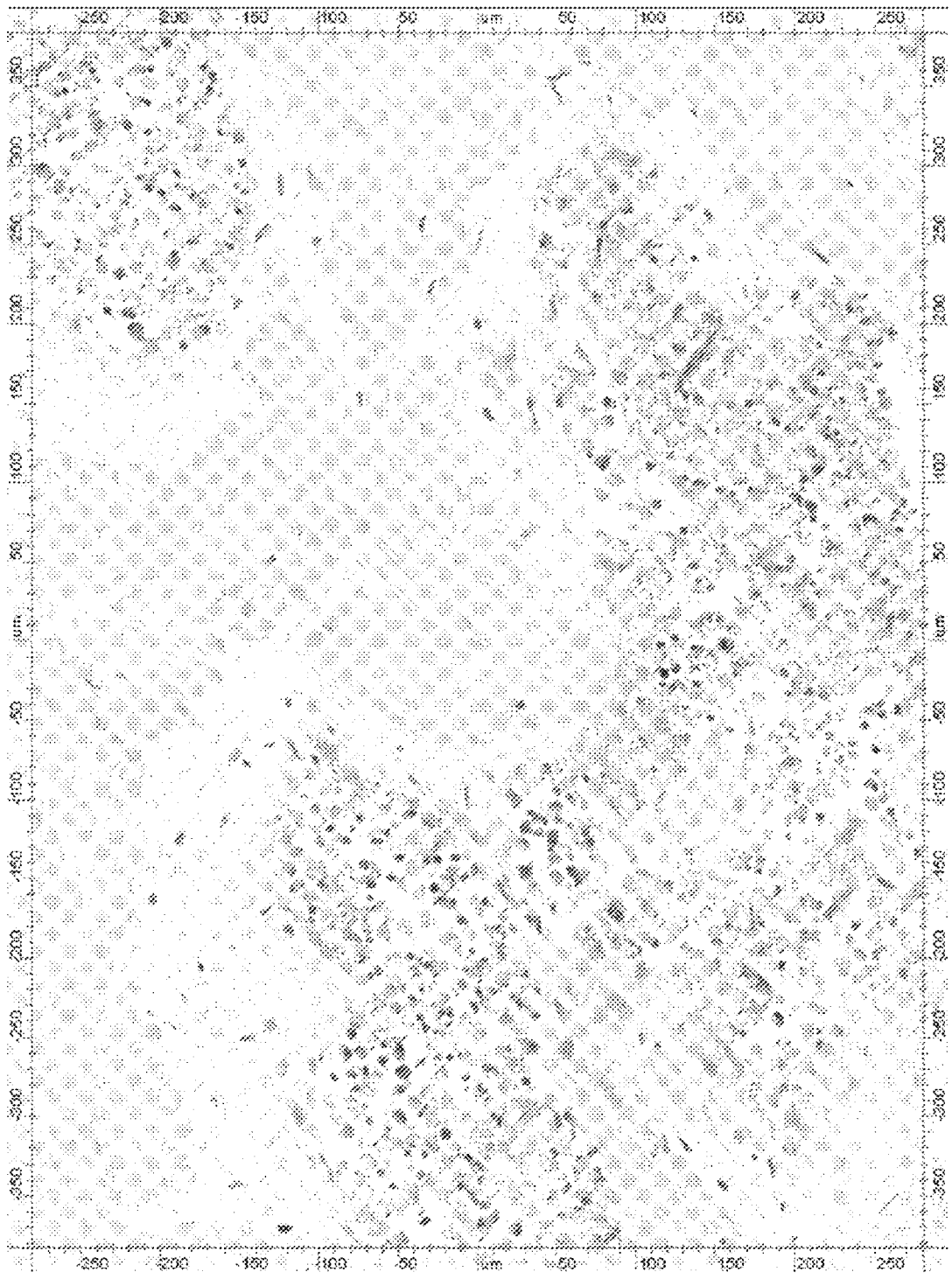
FIG. 11: 10× magnification H&E of cardiomyocyte seeded 3DFC orientated horizontally. The large cellular bundles consist of cardiomyocytes situated between vicryl fibers.

Echocardiography and Hemodynamics: Rats were infarcted using standard techniques in our laboratory. In short, a permanent ligature was placed around the left coronary artery of rats and the animals allowed to recover for three weeks. During this recovery time, rats developed chronic heart failure (CHF); classically defined as depressed ejection fraction and cardiac output, elevated end-diastolic pressure and volume with increased left ventricular chamber dimensions. Chronic heart failure rats were divided at random into control (no treatment) and treatment (cardiomyocyte seeded 3DFC) groups 3 weeks after coronary ligation. Both control and treatment groups were studied at baseline, seeded 3DFC was applied 3 weeks post MI, and studied all rats were studied 6 weeks post MI (3 weeks post implant of seeded 3DFC). Rats received 3 and 6 week echocardiography in addition to 6 week hemodynamics. (FIG. 5-7)

Graphical data of these (EF, CI, EDP) show changes/improvements with statistical (p<0.05) analysis between groups as denoted. Data were expressed as mean±standard error (SE). For the physiologic and echocardiographic measurements, the Student t test was used for single comparison of sham versus other study groups. Interactions were tested using two-way analysis of variance (ANOVA), intergroup differences were evaluated using the Student-Newman-Keuls test for statistical significance (P≤0.05).

Using methods previously described, cardiomyocytes were isolated and seeded onto the 3DFC and incubated overnight. Cardiomyocyte seeded 3DFC were then sutured directly onto the epicardial portion of the rat's infarcted left ventricle. The rat's chest was closed and the animal allowed to recover. Echocardiography data demonstrates improvements in ejection fraction (25%) and cardiac output (55%) in treated vs. non-treated rats (FIGS. 5 & 6), thus demonstrating the use of the constructs of the invention for treating CHF.

We claim:

1. A method for treating a disorder characterized by a lack of functioning cardiomyocytes, comprising contacting the heart of a subject suffering from such a disorder with an amount effective to treat the disorder of a construct comprising cardiomyocytes, cardiac stem cells, or progenitors thereof adhered to a three dimensional fibroblast construct (3DFC), wherein the construct is capable of spontaneous synchronized contractions across the 3DFC; and wherein the cardiomyocytes, cardiac stem cells, or progenitors thereof are seeded on the construct at a density of between $0.5 \times 10^6$ cells/cm$^2$ and $5 \times 10^6$ cells/cm$^2$ and/or the cardiomyocytes, cardiac stem cells, or progenitors thereof are present in a ratio of between about 1:10 and about 10:1 with fibroblasts on the 3DFC:

wherein the cardiomyocytes, cardiac stem cells, or progenitors thereof adhered as a 1-2 cell thick layer over a layer of fibroblasts on
(a) the top surface of the 3DFC, wherein the bottom surface of the 3DFC does not have cardiomvocvtes, cardiac stem cells, or progenitors thereof adhered to it,
(b) the bottom surface of the 3DFC, wherein the top surface of the 3DFC does not have cardiomyocytes, cardiac stem cells, or progenitors thereof adhered to it; or
(c) the top and the bottom surface of the 3DFC.

2. The method of claim 1, wherein the disorder is selected from the group consisting of chronic heart failure (CHF), ischemia without heart failure, cardiomyopathy, dilated cardiomyopathy (DCM), cardiac arrest, congestive heart failure, stable angina, unstable angina, myocardial infarction, coronary artery disease, valvular heart disease, ischemic heart disease, reduced ejection fraction, reduced myocardial perfusion, maladaptive cardiac remodeling, left ventricle remodeling, reduced left ventricle function, left heart failure, right heart failure, backward heart failure, forward heart failure, systolic dysfunction, diastolic dysfunction, systemic vascular resistance, low-output heart failure, high-output heart failure, dyspnea on exertion, dyspnea at rest, orthopnea, tachypnea, paroxysmal nocturnal dyspnea, dizziness, confusion, cool extremities at rest, exercise intolerance, easy fatigueability, peripheral edema, nocturia, ascites, hepatomegaly, pulmonary edema, cyanosis, laterally displaced apex beat, gallop rhythm, heart murmurs, parasternal heave, and pleural effusion.

3. The method of claim 2, where the disorder comprises CHF.

4. The method of claim 2, where the disorder comprises DCM.

5. The method of claim 2, where the disorder comprises left heart failure.

6. The method of claim 2, where the disorder comprises reduced left ventricular function.

7. The method of claim 2, where the disorder comprises right heart failure.

8. The method of claim 1, wherein the construct is attached to the epicardium.

9. The method of claim 8, wherein the construct is non-contracting at the time of contacting with the subject's heart.

10. The method of claim 1, wherein the contacting comprises contacting the construct to the subject's left ventricle.

11. The method of claim 1, further comprising contacting the subject's heart with one or more of thymosin beta-4 (TB4), akt murine thyoma viral oncogene homolog (AKT1), stroma cell-derived factor-1 alpha (SDF-1), and hepatocyte growth factor (HGF).

12. The method of claim 1, wherein the treating comprises one or more of improving left ventricular function, fall in end diastolic pressure (EDP), improving myocardial perfusion, repopulating of the heart's anterior wall with cardiomyocytes, and reversing maladaptive left ventricle remodeling in CHF subjects.

13. The method of claim 1, wherein the cardiomyocytes or cardiac stem cells are present on the construct in a ratio between about 1:10 and about 10:1 fibroblasts.

14. The method of claim 1, herein the cardiomyocytes or cardiac stem cells are seeded on the construct at a density of between $1.3 \times 10^6$ cells/cm$^2$ and $5 \times 10^6$ cells/cm$^2$.

15. The method of claim 1, wherein the cardiomyocytes or cardiac stem cells are seeded on the construct at a density of between $1.5 \times 10^6$ cells/cm$^2$ and $3 \times 10^6$ cells/cm$^2$.

16. The method of claim 1, wherein the cardiomyocytes or cardiac stem cells are of human origin.

17. The method of claim 1, where the disorder comprises reduced ventricular function.

* * * * *

SEQUENCE LISTING

```
<160> NUMBER OF SEQ ID NOS: 11

<210> SEQ ID NO 1
<211> LENGTH: 480
<212> TYPE: PRT
<213> ORGANISM: Homo sapiens

<400> SEQUENCE: 1

Met Ser Asp Val Ala Ile Val Lys Glu Gly Trp Leu His Lys Arg Gly
1               5                   10                  15
```

```
Glu Tyr Ile Lys Thr Trp Arg Pro Arg Tyr Phe Leu Leu Lys Asn Asp
            20                  25                  30

Gly Thr Phe Ile Gly Tyr Lys Glu Arg Pro Gln Asp Val Asp Gln Arg
        35                  40                  45

Glu Ala Pro Leu Asn Asn Phe Ser Val Ala Gln Cys Gln Leu Met Lys
50                      55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
                100                 105                 110

Gln Glu Glu Glu Glu Met Asp Phe Arg Ser Gly Ser Pro Ser Asp Asn
                115                 120                 125

Ser Gly Ala Glu Glu Met Glu Val Ser Leu Ala Lys Pro Lys His Arg
130                     135                 140

Val Thr Met Asn Glu Phe Glu Tyr Leu Lys Leu Leu Gly Lys Gly Thr
145                     150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
                180                 185                 190

Ala His Thr Leu Thr Glu Asn Arg Val Leu Gln Asn Ser Arg His Pro
                195                 200                 205

Phe Leu Thr Ala Leu Lys Tyr Ser Phe Gln Thr His Asp Arg Leu Cys
                210                 215                 220

Phe Val Met Glu Tyr Ala Asn Gly Gly Glu Leu Phe Phe His Leu Ser
225                     230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
                260                 265                 270

Arg Asp Leu Lys Leu Glu Asn Leu Met Leu Asp Lys Asp Gly His Ile
                275                 280                 285

Lys Ile Thr Asp Phe Gly Leu Cys Lys Glu Gly Ile Lys Asp Gly Ala
                290                 295                 300

Thr Met Lys Thr Phe Cys Gly Thr Pro Glu Tyr Leu Ala Pro Glu Val
305                     310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
                340                 345                 350

Asp His Glu Lys Leu Phe Glu Leu Ile Leu Met Glu Glu Ile Arg Phe
                355                 360                 365

Pro Arg Thr Leu Gly Pro Glu Ala Lys Ser Leu Leu Ser Gly Leu Leu
                370                 375                 380

Lys Lys Asp Pro Lys Gln Arg Leu Gly Gly Gly Ser Glu Asp Ala Lys
385                     390                 395                 400

Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
                420                 425                 430
```

Thr Asp Thr Arg Tyr Phe Asp Glu Glu Phe Thr Ala Gln Met Ile Thr
        435                 440                 445

Ile Thr Pro Pro Asp Gln Asp Ser Met Glu Cys Val Asp Ser Glu
    450                 455                 460

Arg Arg Pro His Phe Pro Gln Phe Ser Tyr Ser Ala Ser Gly Thr Ala
465             470                 475                 480

<210> SEQ ID NO 2
<211> LENGTH: 2878
<212> TYPE: DNA
<213> ORGANISM: Homo sapiens

<400> SEQUENCE: 2

| | | |
|---|---|---|
| cggcaggacc gagcgcggca ggcggctggc ccagcgcagc cagcgcggcc cgaaggacgg | 60 |
| gagcaggcgg ccgagcaccg agcgctgggc accgggcacc gagcggcggc ggcacgcgag | 120 |
| gcccggcccc gagcagcgcc cccgcccgcc gcggcctcca gcccggcccc gcccagcgcc | 180 |
| ggcccgcggg gatgcggagc ggcgggcgcc ggaggccgcg gccggctag gcccgcgctc | 240 |
| gcgcccggac gcggcggccc ggggcttagg gaaggccgag ccagcctggg tcaaagaagt | 300 |
| caaagggct gcctggagga ggcagcctgt cagctggtgc atcagaggct gtggccaggc | 360 |
| cagctgggct cggggagcgc cagcctgaga ggagcgcgtg agcgtcgcgg gagcctcggg | 420 |
| caccatgagc gacgtggcta ttgtgaagga gggttggctg cacaaacgag gggagtacat | 480 |
| caagacctgg cggccacgct acttcctcct caagaatgat ggcaccttca ttggctacaa | 540 |
| ggagcggccg caggatgtgg accaacgtga ggctcccctc aacaacttct ctgtggcgca | 600 |
| gtgccagctg atgaagacgg agcggccccg gcccaacacc ttcatcatcc gctgcctgca | 660 |
| gtggaccact gtcatcgaac gcaccttcca tgtggagact cctgaggagc gggaggagtg | 720 |
| gacaaccgcc atccagactg tggctgacgg cctcaagaag caggaggagg aggagatgga | 780 |
| cttccggtcg ggctcacccca gtgacaactc aggggctgaa gagatggagg tgtccctggc | 840 |
| caagcccaag caccgcgtga ccatgaacga gtttgagtac ctgaagctgc tgggcaaggg | 900 |
| cactttcggc aaggtgatcc tggtgaagga gaaggccaca ggccgctact acgccatgaa | 960 |
| gatcctcaag aaggaagtca tcgtggccaa ggacgaggtg gcccacacac tcaccgagaa | 1020 |
| ccgcgtcctg cagaactcca ggcaccccctt cctcacagcc ctgaagtact ctttccagac | 1080 |
| ccacgaccgc ctctgctttg tcatggagta cgccaacggg ggcgagctgt tcttccacct | 1140 |
| gtcccgggag cgtgtgttct ccgaggaccg ggcccgcttc tatggcgctg agattgtgtc | 1200 |
| agccctggac tacctgcact cggagaagaa cgtggtgtac cgggacctca agctggaaaa | 1260 |
| cctcatgctg gacaaggacg ggcacattaa gatcacagac ttcgggctgt gcaaggaggg | 1320 |
| gatcaaggac ggtgccacca tgaagacctt ttgcggcaca cctgagtacc tggcccccga | 1380 |
| ggtgctggag gacaatgact acggccgtgc agtggactgg tggggctgg gcgtggtcat | 1440 |
| gtacgagatg atgtgcggtc gcctgccctt ctacaaccag gaccatgaga agcttttga | 1500 |
| gctcatcctc atggaggaga tccgcttccc gcgcacgctt ggtcccgagg ccaagtcctt | 1560 |
| gctttcaggg ctgctcaaga aggacccaa gcagaggctt ggcggggct ccgaggacgc | 1620 |
| caaggagatc atgcagcatc gcttctttgc cggtatcgtg tggcagcacg tgtacgaaa | 1680 |
| gaagctcagc ccaccccttca agccccaggt cacgtcggag actgacacca ggtattttga | 1740 |
| tgaggagttc acgcccagca tgatcaccat cacaccacct gaccaagatg acagcatgga | 1800 |
| gtgtgtggac agcgagcgca ggccccactt cccccagttc tcctactcgg ccagcggcac | 1860 |

-continued

```
ggcctgaggc ggcggtggac tgcgctggac gatagcttgg agggatggag aggcggcctc    1920
gtgccatgat ctgtatttaa tggttttttat ttctcgggtg catttgagag aagccacgct    1980
gtcctctcga gcccagatgg aaagacgttt ttgtgctgtg ggcagcaccc tcccccgcag    2040
cggggtaggg aagaaaacta tcctgcgggt tttaatttat ttcatccagt ttgttctccg    2100
ggtgtggcct cagccctcag aacaatccga ttcacgtagg gaaatgttaa ggacttctgc    2160
agctatgcgc aatgtggcat tgggggggccg gcaggtcct gcccatgtgt cccctcactc    2220
tgtcagccag ccgccctggg ctgtctgtca ccagctatct gtcatctctc tggggccctg    2280
ggcctcagtt caacctggtg gcaccagatg caacctcact atggtatgct ggccagcacc    2340
ctctcctggg ggtggcaggc acacagcagc cccccagcac taaggccgtg tctctgagga    2400
cgtcatcgga ggctgggccc ctgggatggg accaggatg ggggatgggc cagggtttac    2460
ccagtgggac agaggagcaa ggtttaaatt tgttattgtg tattatgttg ttcaaatgca    2520
ttttgggggt ttttaatctt tgtgacagga aagccctccc ccttcccctt ctgtgtcaca    2580
gttcttggtg actgtcccac cgggagcctc cccctcagat gatctctcca cggtagcact    2640
tgaccttttc gacgcttaac ctttccgctg tcgccccagg ccctccctga ctccctgtgg    2700
gggtggccat ccctgggccc ctccacgcct cctggccaga cgctgccgct gccgctgcac    2760
cacggcgttt ttttacaaca ttcaacttta gtatttttac tattataata taatatggaa    2820
ccttccctcc aaattcttca ataaaagttg cttttcaaaa aaaaaaaaaa aaaaaaa       2878
```

<210> SEQ ID NO 3
<211> LENGTH: 480
<212> TYPE: PRT
<213> ORGANISM: Homo sapiens

<400> SEQUENCE: 3

Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
            20                  25                  30

Gly Thr Phe Ile Gly Tyr Lys Glu Arg Pro Gln Asp Val Asp Gln Arg
        35                  40                  45

Glu Ala Pro Leu Asn Asn Phe Ser Val Ala Gln Cys Gln Leu Met Lys
    50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
            100                 105                 110

Gln Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
    130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro

```
                195                 200                 205
Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
    290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
        355                 360                 365

Pro Arg Thr Leu Gly Pro Glu Ala Lys Ser Leu Leu Ser Gly Leu Leu
    370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
            420                 425                 430

Thr Asp Thr Arg Tyr Phe Asp Glu Glu Phe Thr Ala Gln Met Ile Thr
        435                 440                 445

Ile Thr Pro Pro Asp Gln Asp Asp Ser Met Glu Cys Val Asp Ser Glu
    450                 455                 460

Arg Arg Pro His Phe Pro Gln Phe Ser Tyr Ser Ala Ser Gly Thr Ala
465                 470                 475                 480

<210> SEQ ID NO 4
<211> LENGTH: 2794
<212> TYPE: DNA
<213> ORGANISM: Homo sapiens

<400> SEQUENCE: 4
cggcaggacc gagcgcggca ggcggctggc ccagcgcagc cagcgcggcc cgaaggacgg      60
gagcaggcgg ccgagcaccg agcgctgggc accgggcacc gagcggcggc ggcacgcgag     120
gcccggcccc gagcagcgcc cccgcccgcc gcggcctcca gccgggcccc gcccagcgcc     180
ggcccgcggg gatgcggagc ggcgggcgcc ggaggccgcg gccggctag gcccgcgctc      240 gcgcccggac gcggcggccc gaggctgtgg ccaggccagc tgggctcggg gagcgccagc     300
ctgagaggag cgcgtgagcg tcgcgggagc ctcgggcacc atgagcgacg tggctattgt     360
gaaggagggt tggctgcaca acgaggggga gtacatcaag acctggcggc acgctacttt     420
cctcctcaag aatgatggca ccttcattgg ctacaaggag cggccgcagg atgtggacca     480
acgtgaggct cccctcaaca acttctctgt ggcgcagtgc cagctgatga agacggagcg     540
```

-continued

```
gccccggccc aacaccttca tcatccgctg cctgcagtgg accactgtca tcgaacgcac      600
cttccatgtg gagactcctg aggagcggga ggagtggaca accgccatcc agactgtggc      660
tgacggcctc aagaagcagg aggaggagga gatggacttc cggtcgggct cacccagtga      720
caactcaggg gctgaagaga tggaggtgtc cctggccaag cccaagcacc gcgtgaccat      780
gaacgagttt gagtacctga agctgctggg caagggcact ttcggcaagg tgatcctggt      840
gaaggagaag gccacaggcc gctactacgc catgaagatc ctcaagaagg aagtcatcgt      900
ggccaaggac gaggtggccc acacactcac cgagaaccgc gtcctgcaga actccaggca      960 cccccttcctc acagccctga agtactcttt ccagacccac gaccgcctct gctttgtcat     1020
ggagtacgcc aacgggggcg agctgttctt ccacctgtcc cgggagcgtg tgttctccga     1080
ggaccgggcc cgcttctatg cgctgagat tgtgtcagcc ctggactacc tgcactcgga      1140
gaagaacgtg gtgtaccggg acctcaagct ggagaacctc atgctggaca aggacgggca     1200
cattaagatc acagacttcg ggctgtgcaa ggaggggatc aaggacggtg ccaccatgaa     1260 gacctttgc ggcacacctg agtacctggc ccccgaggtg ctgaggaca atgactacgg       1320 ccgtgcagtg gactggtggg gctgggcgt ggtcatgtac gagatgatgt gcggtcgcct      1380
gcccttctac aaccaggacc atgagaagct ttttgagctc atcctcatgg aggagatccg     1440
cttcccgcgc acgcttggtc ccgaggccaa gtccttgctt tcagggctgc tcaagaagga     1500
ccccaagcag aggcttggcg ggggctccga ggacgcaaag gagatcatgc agcatcgctt     1560
ctttgccggt atcgtgtggc agcacgtgta cgagaagaag ctcagcccac ccttcaagcc     1620
ccaggtcacg tcgagactg acaccaggta ttttgatgag gagttcacgg cccagatgat     1680
caccatcaca ccacctgacc aagatgacag catggagtgt gtggacagcg agcgcaggcc     1740
ccacttcccc cagttctcct actcggccag cggcacggcc tgaggcggcg gtggactgcg     1800
ctggacgata gcttggaggg atggagaggc ggcctcgtgc catgatctgt atttaatggt     1860 tttttatttct cgggtgcatt tgagagaagc cacgctgtcc tctcgagccc agatggaaag    1920
acgtttttgt gctgtgggca gcaccctccc ccgcagcggg gtagggaaga aaactatcct    1980
gcgggtttta atttatttca tccagttttgt tctccgggtg tggcctcagc cctcagaaca    2040
atccgattca cgtagggaaa tgttaaggac ttctgcagct atgcgcaatg tggcattggg     2100
gggccgggca ggtcctgccc atgtgtcccc tcactctgtc agccagccgc cctgggctgt     2160
ctgtcaccag ctatctgtca tctctctggg gccctgggcc tcagttcaac ctggtggcac     2220
cagatgcaac ctcactatgg tatgctggcc agcaccctct cctgggggtg gcaggcacac     2280
agcagccccc cagcactaag gccgtgtctc tgaggacgtc atcggaggct gggcccctgg     2340
gatgggacca gggatggggg atgggccagg gtttacccag tgggacagag gagcaaggtt     2400
taaatttgtt attgtgtatt atgttgttca aatgcatttt gggggttttt aatctttgtg     2460
acaggaaagc cctcccccctt cccctttctgt gtcacagttc ttggtgactg tcccaccggg    2520
agcctccccc tcagatgatc tctccacggt agcacttgac cttttcgacg cttaaccttt     2580
ccgctgtcgc cccaggccct ccctgactcc ctgtgggggt ggccatccct gggcccctcc     2640
acgcctcctg gccagacgct gccgctgccg ctgcaccacg gcgttttttt acaacattca     2700
actttagtat ttttactatt ataatataat atggaacctt ccctccaaat tcttcaataa     2760
aagttgcttt tcaaaaaaaa aaaaaaaaaa aaaa                                  2794
```

<210> SEQ ID NO 5
<211> LENGTH: 480

<212> TYPE: PRT
<213> ORGANISM: Homo sapiens

<400> SEQUENCE: 5

```
Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
            20                  25                  30

Gly Thr Phe Ile Gly Tyr Lys Glu Arg Pro Gln Asp Val Asp Gln Arg
        35                  40                  45

Glu Ala Pro Leu Asn Asn Phe Ser Val Ala Gln Cys Gln Leu Met Lys
    50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
            100                 105                 110

Gln Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
    130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
    290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
        355                 360                 365

Pro Arg Thr Leu Gly Pro Glu Ala Lys Ser Leu Leu Ser Gly Leu Leu
    370                 375                 380

Lys Lys Asp Pro Lys Gln Arg Leu Gly Gly Gly Ser Glu Asp Ala Lys
385                 390                 395                 400
```

```
Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
            420                 425                 430

Thr Asp Thr Arg Tyr Phe Asp Glu Glu Phe Thr Ala Gln Met Ile Thr
        435                 440                 445

Ile Thr Pro Pro Asp Gln Asp Asp Ser Met Glu Cys Val Asp Ser Glu
450                 455                 460

Arg Arg Pro His Phe Pro Gln Phe Ser Tyr Ser Ala Ser Gly Thr Ala
465                 470                 475                 480

<210> SEQ ID NO 6
<211> LENGTH: 3008
<212> TYPE: DNA
<213> ORGANISM: Homo sapiens

<400> SEQUENCE: 6
```

| | | | | | |
|---|---|---|---|---|---|
| taattatggg | tctgtaacca | ccctggactg | ggtgctcctc | actgacggac | ttgtctgaac | 60 |
| ctctctttgt | ctccagcgcc | cagcactggg | cctggcaaaa | cctgagacgc | ccggtacatg | 120 |
| ttggccaaat | gaatgaacca | gattcagacc | ggcaggggcg | ctgtggttta | ggagggggcct | 180 |
| ggggtttctc | ccaggaggtt | tttgggcttg | cgctggaggg | ctctggactc | ccgtttgcgc | 240 |
| cagtggcctg | catcctggtc | ctgtcttcct | catgtttgaa | tttctttgct | ttcctagtct | 300 |
| ggggagcagg | gaggagccct | gtgccctgtc | ccaggatcca | tgggtaggaa | caccatggac | 360 |
| agggagagca | aacggggcca | tctgtcacca | ggggcttagg | gaaggccgag | ccagcctggg | 420 |
| tcaaagaagt | caaggggct | gcctggagga | ggcagcctgt | cagctggtgc | atcagaggct | 480 |
| gtggccaggc | cagctgggct | cggggagcgc | cagcctgaga | ggagcgcgtg | agcgtcgcgg | 540 |
| gagcctcggg | caccatgagc | gacgtggcta | ttgtgaagga | gggttggctg | cacaaacgag | 600 |
| gggagtacat | caagacctgg | cggccacgct | acttcctcct | caagaatgat | ggcaccttca | 660 |
| ttggctacaa | ggagcggccg | caggatgtgg | accaacgtga | ggctccctc | aacaacttct | 720 |
| ctgtggcgca | gtgccagctg | atgaagacg | agcggccccg | gcccaacacc | ttcatcatcc | 780 |
| gctgcctgca | gtggaccact | gtcatcgaac | gcaccttcca | tgtggagact | cctgaggagc | 840 |
| gggaggagtg | gacaaccgcc | atccagactg | tggctgacgg | cctcaagaag | caggaggagg | 900 |
| aggagatgga | cttccggtcg | ggctcaccca | gtgacaactc | agggctgaa | gagatggagg | 960 |
| tgtccctggc | caagcccaag | caccgcgtga | ccatgaacga | gtttgagtac | ctgaagctgc | 1020 |
| tgggcaaggg | cactttcggc | aaggtgatcc | tggtgaagga | gaaggccaca | ggccgctact | 1080 |
| acgccatgaa | gatcctcaag | aaggaagtca | tcgtggccaa | ggacgaggtg | gcccacacac | 1140 |
| tcaccgagaa | ccgcgtcctg | cagaactcca | ggcaccccctt | cctcacagcc | ctgaagtact | 1200 |
| ctttccagac | ccacgaccgc | ctctgctttg | tcatggagta | cgccaacggg | ggcgagctgt | 1260 |
| tcttccacct | gtcccgggag | cgtgtgttct | ccgaggaccg | ggcccgcttc | tatgcgcctg | 1320 |
| agattgtgtc | agccctggac | tacctgcact | cggagaagaa | cgtggtgtac | cgggacctca | 1380 |
| agctggagaa | cctcatgctg | acaaggacg | ggcacattaa | gatcacagac | ttcgggctgt | 1440 |
| gcaaggaggg | gatcaaggac | ggtgccacca | tgaagacctt | ttgcggcaca | cctgagtacc | 1500 |
| tggcccccga | ggtgctggag | acaatgact | acgccgtgc | agtggactgg | tggggctgg | 1560 |
| gcgtggtcat | gtacgagatg | atgtgcggtc | gcctgccctt | ctacaaccag | gaccatgaga | 1620 |
| agcttttga | gctcatcctc | atggaggaga | tccgcttccc | gcgcacgctt | ggtcccgagg | 1680 |

```
ccaagtcctt gctttcaggg ctgctcaaga aggaccccaa gcagaggctt ggcggggct      1740 ccgaggacgc caaggagatc atgcagcatc gcttctttgc cggtatcgtg tggcagcacg      1800
tgtacgagaa gaagctcagc ccacccttca agccccaggt cacgtcggag actgacacca      1860
ggtattttga tgaggagttc acggcccaga tgatcaccat cacaccacct gaccaagatg      1920
acagcatgga gtgtgtggac agcgagcgca ggccccactt cccccagttc tcctactcgg      1980
ccagcggcac ggcctgaggc ggcggtggac tgcgctggac gatagcttgg agggatggag      2040
aggcggcctc gtgccatgat ctgtatttaa tggttttttat ttctcgggtg catttgagag      2100
aagccacgct gtcctctcga gcccagatgg aaagacgttt ttgtgctgtg ggcagcaccc      2160
tcccccgcag cggggtaggg aagaaaacta tcctgcgggt tttaatttat ttcatccagt      2220 tgttctccg ggtgtggcct cagccctcag aacaatccga ttcacgtagg gaaatgttaa      2280
ggacttctgc agctatgcgc aatgtggcat tggggggccg ggcaggtcct gcccatgtgt      2340
cccctcactc tgtcagccag ccgccctggg ctgtctgtca ccagctatct gtcatctctc      2400
tggggccctg ggcctcagtt caacctggtg gcaccagatg caacctcact atggtatgct      2460
ggccagcacc ctctcctggg ggtggcaggc acacagcagc cccccagcac taaggccgtg      2520
tctctgagga cgtcatcgga ggctgggccc ctgggatggg accagggatg ggggatgggc      2580
cagggtttac ccagtgggac agaggagcaa ggtttaaatt tgttattgtg tattatgttg      2640
ttcaaatgca ttttggggt ttttaatctt tgtgacagga aagccctccc ccttccccctt      2700 ctgtgtcaca gttcttggtg actgtcccac cgggagcctc cccctcagat gatctctcca      2760
cggtagcact tgaccttttc gacgcttaac ctttccgctg tcgccccagg ccctccctga      2820
ctccctgtgg gggtggccat ccctgggccc ctccacgcct cctggccaga cgctgccgct      2880
gccgctgcac cacggcgttt ttttacaaca ttcaacttta gtattttttac tattataata      2940 taatatggaa ccttccctcc aaattcttca ataaaagttg cttttcaaaa aaaaaaaaa      3000 aaaaaaaa                                                              3008
```

<210> SEQ ID NO 7
<211> LENGTH: 71
<212> TYPE: PRT
<213> ORGANISM: Homo sapiens

<400> SEQUENCE: 7

Ser Asp Tyr Lys Pro Val Ser Leu Ser Tyr Arg Cys Pro Cys Arg Phe
1               5                   10                  15

Phe Glu Ser His Val Ala Arg Ala Asn Val Lys His Leu Lys Ile Leu
            20                  25                  30

Asn Thr Pro Asn Cys Ala Leu Gln Ile Val Ala Arg Leu Lys Asn Asn
        35                  40                  45

Asn Arg Gln Val Cys Ile Asp Pro Lys Leu Lys Trp Ile Gln Glu Tyr
    50                  55                  60

Leu Glu Lys Ala Leu Asn Lys
65                  70

<210> SEQ ID NO 8
<211> LENGTH: 97
<212> TYPE: PRT
<213> ORGANISM: Homo sapiens

<400> SEQUENCE: 8

Gly Gln Arg Lys Arg Arg Asn Thr Ile His Glu Phe Lys Lys Ser Ala

|   1 |     |     |     | 5   |     |     |     |     | 10  |     |     |     |     | 15  |
|-----|-----|-----|-----|-----|-----|-----|-----|-----|-----|-----|-----|-----|-----|-----|

Lys Thr Thr Leu Ile Lys Ile Asp Pro Ala Leu Lys Ile Lys Thr Lys
                20                  25                  30

Lys Val Asn Thr Ala Asp Gln Cys Ala Asn Arg Cys Thr Arg Asn Lys
            35                  40                  45

Gly Leu Pro Phe Thr Cys Lys Ala Phe Val Phe Asp Lys Ala Arg Lys
        50                  55                  60

Gln Cys Leu Trp Phe Pro Phe Asn Ser Met Ser Ser Gly Val Lys Lys
65                  70                  75                  80

Glu Phe Gly His Glu Phe Asp Leu Tyr Glu Asn Lys Asp Tyr Ile Arg
                85                  90                  95

Asn

<210> SEQ ID NO 9
<211> LENGTH: 193
<212> TYPE: PRT
<213> ORGANISM: Homo sapiens

<400> SEQUENCE: 9

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Pro Arg Leu
                20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
        50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
        130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
                180                 185                 190

Arg

<210> SEQ ID NO 10
<211> LENGTH: 3398
<212> TYPE: DNA
<213> ORGANISM: Homo sapiens

<400> SEQUENCE: 10
agcttctggg cttccagacc cagctacttt gcggaactca gcaacccagg catctctgag     60
tctccgccca agaccgggat gccccccagg aggtgtccgg gagcccagcc tttcccagat    120
agcagctccg ccagtcccaa gggtgcgcaa ccggctgcac tcccctcccg cgacccaggg    180

```
cccgggagca gccccccatga cccacacgca cgtctgcagc agccccgtca gccccggagc      240
ctcaacccag gcgtcctgcc cctgctctga cccccgggtgg cccctacccc tggcgacccc     300
tcacgcacac agcctctccc ccaccccccac ccgcgcacgc acacatgcag ataacagccc     360 cgaccccccgg ccagagccgc agagtccctg ggccaccccg gccgctcgct gcgctgcgcc    420
gcaccgcgct gtcctcccgg agccggaccg gggccaccgc gcccgctctg ctccgacacc     480 gcgcccctg dacagccgcc ctctcctcca ggcccgtggg gctggccctg caccgccgag      540
cttcccggga tgagggcccc cggtgtggtc accggcgcc ccaggtcgct gagggacccc      600
ggccaggcgc ggagatgggg gtgcacggtg agtactcgcg ggctgggcgc tcccgccccgc    660 ccgggtccct gtttgagcgg ggatttagcg ccccggctat tggccaggag gtggctgggt     720
tcaaggaccg gcgacttgtc aaggaccccg gaaggggag gggggtgggg cagcctccac      780
gtgccagcgg ggacttgggg gagtccttgg ggatggcaaa aacctgacct gtgaagggga     840
cacagtttgg gggttgaggg gaagaaggtt tgggggttc tgctgtgcca gtggagagga     900
agctgataag ctgataacct gggcgctgga gccaccactt atctgccaga ggggaagcct    960
ctgtcacacc aggattgaag tttggccgga gaagtggatg ctggtagcct gggggtgggg   1020
tgtgcacacg gcagcaggat tgaatgaagg ccagggaggc agcacctgag tgcttgcatg    1080
gttggggaca ggaaggacga gctggggcag agacgtgggg atgaaggaag ctgtccttcc    1140
acagccaccc ttctccctcc ccgcctgact ctcagcctgg ctatctgttc tagaatgtcc    1200
tgcctggctg tggcttctcc tgtccctgct gtcgctccct ctgggcctcc cagtcctggg    1260
cgccccacca cgcctcatct gtgacagccg agtcctgcag aggtacctct tggaggccaa    1320
ggaggccgag aatatcacgg tgagacccct tccccagcac attccacaga actcacgctc    1380
agggcttcag ggaactcctc ccagatccag gaacctggca cttggtttgg ggtggagttg    1440
ggaagctaga cactgccccc ctacataaga ataagtctgg tggccccaaa ccatacctgg    1500
aaactaggca aggagcaaag ccagcagatc ctacgcctgt ggccagggcc agagccttca    1560 gggaccccttg actccccggg ctgtgtgcat ttcagacggg ctgtgctgaa cactgcagct    1620
tgaatgagaa tatcactgtc ccagacacca aagttaattt ctatgcctgg aagaggatgg    1680
aggtgagttc cttttttttt tttttttcctt tcttttggag aatctcattt gcgagcctga   1740
ttttggatga aagggagaat gatcgaggga aaggtaaaat ggagcagcag agatgaggct    1800
gcctgggcgc agaggctcac gtctataatc ccaggctgag atggccgaga tgggagaatt    1860
gcttgagccc tggagtttca gaccaaccta ggcagcatag tgagatcccc catctctaca   1920
aacatttaaa aaaattagtc aggtgaagtg gtgcatggtg gtagtcccag atatttggaa   1980
ggctgaggcg ggaggatcgc ttgagcccag gaatttgagg ctgcagtgag ctgtgatcac    2040
accactgcac tccagcctca gtgacagagt gaggccctgt ctcaaaaaag aaaagaaaaa   2100
agaaaaataa tgagggctgt atggaatacg ttcattattc attcactcac tcactcactc   2160
attcattcat tcattcattc aacaagtctt attgcatacc ttctgtttgc tcagcttggt   2220
gcttggggct gctgaggggc aggagggaga gggtgacatc cctcagctga ctcccagagt   2280
ccactccctg taggtcgggc agcaggccgt agaagtctgg cagggcctgg ccctgctgtc   2340
ggaagctgtc ctgcggggcc aggccctgtt ggtcaactct tcccagccgt gggagcccct   2400
gcagctgcat gtggataaag ccgtcagtgg ccttcgcagc ctcaccactc tgcttcgggc   2460
tctgggagcc caggtgagta ggagcggaca cttctgcttg cccttttctgt aagagggga   2520 gaagggtctt gctaaggagt acaggaactg tccgtattcc ttcccttttct gtggcactgc   2580
```

```
agcgacctcc tgttttctcc ttggcagaag gaagccatct cccctccaga tgcggcctca    2640
gctgctccac tccgaacaat cactgctgac actttccgca aactcttccg agtctactcc    2700
aatttcctcc ggggaaagct gaagctgtac acaggggagg cctgcaggac aggggacaga    2760
tgaccaggtg tgtccacctg gcatatcca ccacctccct caccaacatt gcttgtgcca    2820
caccctcccc cgccactcct gaaccccgtc gaggggctct cagctcagcg ccagcctgtc    2880
ccatggacac tccagtgcca ccaatgacat ctcaggggcc agaggaactg tccagagagc    2940
aactctgaga tctaaggatg tcacagggcc aacttgaggg cccagagcag gaagcattca    3000
gagagcagct ttaaactcag ggacagaccc atgctgggaa gacgcctgag ctcactcggc    3060
accctgcaaa attgatgcca ggacacgctt tggaggcgat ttacctgttt tcgcacctac    3120
catcagggac aggatgacct ggagaactta ggtggcaagc tgtgacttct ccaggtctca    3180
cgggcatggg cactcccttg gtggcaagag ccccctttgac accggggtgg tgggaaccat    3240
gaagacagga tggggctgg cctctggctc tcatggggtc caacttttgt gtattcttca    3300
acctcattga caagaactga aaccaccaat atgactcttg gcttttctgt tttctgggaa    3360
cctccaaatc ccctggctct gtcccactcc tggcagca                            3398
```

<210> SEQ ID NO 11
<211> LENGTH: 44
<212> TYPE: PRT
<213> ORGANISM: Homo sapiens

<400> SEQUENCE: 11

```
Met Ser Asp Lys Pro Asp Met Ala Glu Ile Glu Lys Phe Asp Lys Ser
1               5                   10                  15

Lys Leu Lys Lys Thr Glu Thr Gln Glu Lys Asn Pro Leu Pro Ser Lys
            20                  25                  30

Glu Thr Ile Glu Gln Glu Lys Gln Ala Gly Glu Ser
        35                  40
```